US008721640B2

(12) United States Patent
Taylor et al.

(10) Patent No.: US 8,721,640 B2
(45) Date of Patent: May 13, 2014

(54) ENDOSCOPIC VESSEL SEALER AND DIVIDER HAVING A FLEXIBLE ARTICULATING SHAFT

(75) Inventors: Eric Taylor, Middletown, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 794 days.

(21) Appl. No.: 12/443,095

(22) PCT Filed: Oct. 5, 2007

(86) PCT No.: PCT/US2007/021438
§ 371 (c)(1),
(2), (4) Date: Mar. 26, 2009

(87) PCT Pub. No.: WO2008/045348
PCT Pub. Date: Apr. 17, 2008

(65) Prior Publication Data
US 2010/0076433 A1 Mar. 25, 2010

Related U.S. Application Data

(60) Provisional application No. 60/850,214, filed on Oct. 6, 2006.

(51) Int. Cl.
*A61B 18/18* (2006.01)
*A61B 17/32* (2006.01)
(52) U.S. Cl.
USPC .............................................. 606/51; 606/171
(58) Field of Classification Search
USPC ................. 606/52, 170, 171, 48, 51, 205–208
See application file for complete search history.

(56) References Cited

U.S. PATENT DOCUMENTS 1,822,330 A  9/1931 Ainslie
2,327,353 A  8/1943 Karle
(Continued)

FOREIGN PATENT DOCUMENTS

JP         8224241 A     9/1996
WO    WO 2008/045333    4/2008
WO    WO 2008/045374    4/2008

OTHER PUBLICATIONS

International Search Report for PCT/US07/021438 date of completion is Jan. 25, 2008 (3 pages).

(Continued)

*Primary Examiner* — Theodore Stigell
*Assistant Examiner* — Weng Lee

(57) ABSTRACT

An electrosurgical instrument for treating tissue includes a housing having a flexible shaft extending therefrom having an axis A-A defined therethrough. The flexible shaft has first and second jaw members attached at a distal end thereof and each jaw member includes an electrically conductive tissue contacting surface adapted to connect to a source of electrosurgical energy such that the electrically conductive tissue contacting surfaces are capable of conducting electrosurgical energy through tissue held therebetween. A drive assembly is disposed in the housing and has a first actuator operably coupled to a drive rod for reciprocation thereof and a second actuator operably coupled to the drive rod for rotation thereof. A knife is operably coupled to a distal end of the drive rod. Actuation of the first actuator moves the jaw members relative to one another for engaging tissue and actuation of the second actuator rotates the drive rod about the axis A-A to translate the knife to cut tissue disposed between the jaw members.

17 Claims, 29 Drawing Sheets

(56) References Cited

U.S. PATENT DOCUMENTS

| | | | |
|---|---|---|---|
| 3,073,311 A | 1/1963 | Tibbs et al. | |
| 4,236,470 A | 12/1980 | Stenson | |
| 4,829,313 A | 5/1989 | Taggart | |
| 5,037,433 A | 8/1991 | Wilk et al. | |
| 5,042,707 A | 8/1991 | Taheri | |
| 5,100,430 A | 3/1992 | Avellanet et al. | |
| 5,146,921 A * | 9/1992 | Terwilliger et al. | 600/567 |
| 5,209,747 A | 5/1993 | Knoepfler | |
| 5,300,082 A | 4/1994 | Sharpe et al. | |
| 5,308,353 A | 5/1994 | Beurrier | |
| 5,314,445 A | 5/1994 | Heidmueller née Degwitz et al. | |
| 5,330,502 A | 7/1994 | Hassler et al. | |
| 5,350,391 A | 9/1994 | Iacovelli | |
| 5,374,277 A | 12/1994 | Hassler | |
| 5,389,103 A | 2/1995 | Melzer et al. | |
| 5,403,342 A | 4/1995 | Tovey et al. | |
| 5,439,478 A | 8/1995 | Palmer | |
| 5,454,823 A | 10/1995 | Richardson et al. | |
| 5,454,827 A | 10/1995 | Aust et al. | |
| 5,480,406 A | 1/1996 | Nolan et al. | |
| 5,540,706 A | 7/1996 | Aust et al. | |
| 5,564,615 A | 10/1996 | Bishop et al. | |
| 5,575,799 A | 11/1996 | Bolanos et al. | |
| 5,582,611 A | 12/1996 | Tsuruta et al. | |
| 5,582,617 A | 12/1996 | Klieman et al. | |
| 5,591,181 A | 1/1997 | Stone et al. | |
| 5,601,224 A | 2/1997 | Bishop et al. | |
| 5,620,415 A | 4/1997 | Lucey et al. | |
| 5,674,229 A | 10/1997 | Tovey et al. | |
| 5,690,652 A | 11/1997 | Wurster et al. | |
| 5,690,653 A | 11/1997 | Richardson et al. | |
| 5,752,973 A | 5/1998 | Kieturakis | |
| 5,759,188 A | 6/1998 | Yoon | |
| 5,766,196 A | 6/1998 | Griffiths | |
| 5,779,646 A | 7/1998 | Koblish et al. | |
| 5,792,165 A | 8/1998 | Klieman et al. | |
| 5,797,537 A | 8/1998 | Oberlin et al. | |
| 5,797,927 A | 8/1998 | Yoon | |
| 5,814,054 A | 9/1998 | Kortenbach et al. | |
| 5,817,119 A | 10/1998 | Klieman et al. | |
| 5,827,323 A | 10/1998 | Klieman et al. | |
| 5,876,412 A | 3/1999 | Piraka | |
| 5,897,563 A | 4/1999 | Yoon et al. | |
| 5,906,630 A | 5/1999 | Anderhub et al. | |
| 5,928,136 A | 7/1999 | Barry | |
| 5,954,731 A | 9/1999 | Yoon | |
| 5,954,733 A | 9/1999 | Yoon | |
| 5,957,937 A | 9/1999 | Yoon | |
| 5,984,932 A | 11/1999 | Yoon | |
| 5,993,466 A | 11/1999 | Yoon | |
| 5,993,467 A | 11/1999 | Yoon | |
| 5,997,565 A | 12/1999 | Inoue | |
| 6,004,332 A | 12/1999 | Yoon et al. | |
| 6,017,358 A | 1/2000 | Yoon et al. | |
| 6,027,522 A | 2/2000 | Palmer | |
| 6,077,287 A | 6/2000 | Taylor et al. | |
| 6,080,180 A | 6/2000 | Yoon | |
| 6,086,601 A | 7/2000 | Yoon | |
| 6,126,665 A | 10/2000 | Yoon | |
| 6,139,563 A | 10/2000 | Cosgrove, III et al. | |
| 6,143,005 A | 11/2000 | Yoon et al. | |
| 6,171,316 B1 | 1/2001 | Kovac et al. | |
| 6,206,893 B1 | 3/2001 | Klein et al. | |
| 6,214,028 B1 | 4/2001 | Yoon et al. | |
| 6,223,100 B1 | 4/2001 | Green | |
| 6,224,614 B1 | 5/2001 | Yoon | |
| 6,261,307 B1 | 7/2001 | Yoon et al. | |
| 6,319,262 B1 | 11/2001 | Bates et al. | |
| 6,358,259 B1 | 3/2002 | Swain et al. | |
| 6,494,888 B1 | 12/2002 | Laufer et al. | |
| 6,506,196 B1 | 1/2003 | Laufer | |
| 6,517,539 B1 | 2/2003 | Smith et al. | |
| 6,569,105 B1 | 5/2003 | Kortenbach et al. | |
| 6,582,450 B2 | 6/2003 | Ouchi | |
| 6,638,287 B2 | 10/2003 | Danitz et al. | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,676,676 B2 | 1/2004 | Danitz et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,773,441 B1 | 8/2004 | Laufer et al. | |
| 6,821,285 B2 | 11/2004 | Laufer et al. | |
| 6,835,200 B2 | 12/2004 | Laufer et al. | |
| 6,889,116 B2 | 5/2005 | Jinno | |
| 6,936,061 B2 | 8/2005 | Sasaki | |
| 6,972,017 B2 | 12/2005 | Smith et al. | |
| 6,981,628 B2 | 1/2006 | Wales | |
| 6,997,931 B2 | 2/2006 | Sauer et al. | |
| 7,052,489 B2 | 5/2006 | Griego et al. | |
| 7,063,715 B2 | 6/2006 | Onuki et al. | |
| 7,107,124 B2 | 9/2006 | Green | |
| 7,153,314 B2 | 12/2006 | Laufer et al. | |
| 7,248,944 B2 | 7/2007 | Green | |
| 2001/0018591 A1 * | 8/2001 | Brock et al. | 606/130 |
| 2002/0188294 A1 * | 12/2002 | Couture et al. | 606/51 |
| 2003/0083684 A1 | 5/2003 | Cesarini et al. | |
| 2004/0116924 A1 | 6/2004 | Dycus et al. | |
| 2004/0243125 A1 | 12/2004 | Dycus et al. | |
| 2006/0064085 A1 | 3/2006 | Schechter et al. | |
| 2006/0074407 A1 | 4/2006 | Padget et al. | |
| 2006/0253126 A1 | 11/2006 | Bjerken et al. | |
| 2006/0282096 A1 | 12/2006 | Shelton, IV et al. | |

OTHER PUBLICATIONS

International Search Report, Publication No. WO 200/045350 dated Apr. 8, 2008.
European Search Report EP0783310 dated Dec. 11, 2012.
European Search Report for EP 12198952.9-1652 date of completion is Feb. 28, 2013 (7 pages).
European Search Report for EP 07839309.7-2305 date of completion is Feb. 8, 2012 (3 pages).
Extended European Search Report corresponding to EP 10 75 1212.1-1652, completed Jan. 22, 2014 and mailed Jan. 31, 2014; (9 pp).

* cited by examiner

ENDOSCOPIC VESSEL SEALER AND DIVIDER HAVING A FLEXIBLE ARTICULATING SHAFT

CROSS REFERENCE TO RELATED APPLICATION

This application is a National Stage Application of PCT/US2007/021438 filed Oct. 5, 2007 under 35USC §371 (a), which claims benefit of and priority to U.S. Provisional Patent Application Ser. No. 60/850,214 filed Oct. 6, 2006 the disclosures of each of the above-identified applications are hereby incorporated by reference in their entirety.

BACKGROUND

The present disclosure relates to an electrosurgical forceps and more particularly, the present disclosure relates to an endoscopic electrosurgical forceps for sealing and/or cutting tissue utilizing an elongated, generally flexible and articulating shaft.

TECHNICAL FIELD

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed.

Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss.

In continuing efforts to reduce the trauma of surgery, interest has recently developed in the possibilities of performing procedures to diagnose and surgically treat a medical condition without any incision in the abdominal wall by using a natural orifice (e.g., the mouth or anus) to access the target tissue. Such procedures are sometimes referred to as endoluminal procedures, transluminal procedures, or natural orifice transluminal endoscopic surgery ("NOTES"). Although many such endoluminal procedures are still being developed, they generally utilize a flexible endoscope instrument or flexible catheter to provide access to the tissue target tissue. Endoluminal procedures have been used to treat conditions within the lumen including for example, treatment of gastroesophageal reflux disease in the esophagus and removal of polyps from the colon. In some instances, physicians have gone beyond the luminal confines of the gastrointestinal tract to perform intra-abdominal procedures. For example, using flexible endoscopic instrumentation, the wall of the stomach can be punctured and an endoscope advanced into the peritoneal cavity to perform various procedures.

Using such endoluminal techniques, diagnostic exploration, liver biopsy, cholecystectomy, splenectomy, and tubal ligation have reportedly been performed in animal models. After the intra-abdominal intervention is completed, the endoscopic instrumentation is retracted into the stomach and the puncture closed. Other natural orifices, such as the anus or vagina, may also allow access to the peritoneal cavity.

As mentioned above, many endoscopic and endoluminal surgical procedures typically require cutting or ligating blood vessels or vascular tissue. However, this ultimately presents a design challenge to instrument manufacturers who must attempt to find ways to make endoscopic instruments that fit through the smaller cannulas. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue utilizing specialized vessel sealing instruments.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure. Moreover, coagulation of large tissue or vessels results in a notoriously weak proximal thrombus having a low burst strength whereas tissue seals have a relatively high burst strength and may be effectively severed along the tissue sealing plane.

More particularly, in order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

It has been found that the pressure range for assuring a consistent and effective seal is between about 3 $kg/cm^2$ to about 16 $kg/cm^2$ and, desirably, within a working range of 7 $kg/cm^2$ to 13 $kg/cm^2$. Manufacturing an instrument which is capable of providing a closure pressure within this working range has been shown to be effective for sealing arteries, tissues and other vascular bundles.

Various force-actuating assemblies have been developed in the past for providing the appropriate closure forces to effect vessel sealing. For example, commonly-owned U.S. patent application Ser. Nos. 10/460,926 and 11/513,979 disclose two different envisioned actuating assemblies developed by Valleylab, Inc. of Boulder, Colo., a division of Tyco Healthcare LP, for use with Valleylab's vessel sealing and dividing instruments commonly sold under the trademark LIGA-SURE®. The contents of both of these applications are hereby incorporated by reference herein.

During use, one noted challenge for surgeons has been the inability to manipulate the end effector assembly of the vessel sealer to grasp tissue in multiple planes, i.e., off-axis, while generating the above-noted required forces to effect a reliable vessel seal. It would therefore be desirable to develop an endoscopic or endoluminal vessel sealing instrument which includes an end effector assembly capable of being manipulated along multiple axes to enable the surgeon to grasp and seal vessels lying along different planes within a surgical cavity.

Endoluminal procedures often require accessing tissue deep in tortuous anatomy of a natural lumen using a flexible catheter or endoscope. Conventional vessel sealing devices may not be appropriate for use in some endoluminal procedures because of a rigid shaft that can not easily negotiate the tortuous anatomy of a natural lumen It would therefore be desirable to develop an endoscopic or endoluminal vessel sealing instrument having a flexible shaft capable of insertion in a flexible endoscope or catheter.

SUMMARY

The present disclosure relates to an electrosurgical instrument for treating tissue which includes a housing having a flexible shaft extending therefrom with an axis A-A defined therethrough. The shaft includes first and second jaw members attached at a distal end thereof each including an electrically conductive tissue contacting surface adapted to connect to a source of electrosurgical energy. Upon electrical activation, the electrically conductive tissue contacting surfaces conduct electrosurgical energy through tissue held between the jaw members. A drive assembly is encased in the housing and includes a first actuator operably coupled to a drive rod for reciprocation thereof and a second actuator operably coupled to the drive rod for rotation thereof. A knife is included and operably coupled to a distal end of the drive rod. Actuation of the first actuator moves the jaw members from a first position in spaced relation to one another to a second position closer to one another for engaging tissue.

Actuation of the second actuator rotates the drive rod about the axis A-A to translate the knife to cut tissue disposed between the jaw members.

In one embodiment, the forceps includes a cam assembly coupled to the distal end of the drive rod. The cam assembly includes a camming hub having a grooved outer periphery defined therein which is configured to matingly engage a corresponding detent disposed on the knife. Rotational movement of the drive rod correspondingly rotates the camming hub which, in turn, translates the detent and knife relative to the jaw members. A coupling device, e.g., a keyed rod, is configured at one end to interface with the drive rod and configured at an opposite end to matingly engage a key-like aperture defined in the camming hub.

In another embodiment, the flexible shaft includes a plurality of joints nestingly arranged in series to form at least a portion of the flexible shaft. Each joint may include one or more lumens defined therethrough for allowing reciprocation of the drive rod therein. In one embodiment, each joint includes a central lumen formed therein and a pair of opposed lumens formed on either side of the central lumen. The electrosurgical instrument may include a pair of articulation cables slideably extendable through the respective opposed lumens which are moveable relative to one another to articulate the shaft relative to axis A-A.

In yet another embodiment, a third actuator may be included which is operably coupled to the housing for moving the pair of articulation cables relative to one another for articulating the flexible shaft relative to axis A-A.

The present disclosure also relates to an electrosurgical instrument for treating tissue which includes a housing having a flexible shaft extending therefrom including an axis A-A defined therethrough. An end effector assembly is attached at the distal end of the shaft which includes a clevis for supporting first and second jaw members about a pivot pin such that the jaw members are moveable relative to one another. Each jaw member includes an electrically conductive tissue contacting surface adapted to connect to a source of electrosurgical energy such that the electrically conductive tissue contacting surfaces are capable of conducting electrosurgical energy through tissue held therebetween. The jaw members each include an angled cam surface defined therein and the clevis includes a slot defined therein. A knife is operably coupled to a distal end of the drive rod and a drive assembly is disposed in the housing. The drive rod assembly includes a first actuator operably coupled to a drive rod for reciprocation thereof and a second actuator operably coupled to the drive rod for rotation thereof. The distal end of the drive rod is configured to receive a drive pin which engages both the cam surface defined in the jaw members and the slot defined in the clevis such that actuation of the first actuator reciprocates the drive pin to move the jaw members from a first position in spaced relation to one another to a second position closer to one another for engaging tissue and actuation of the second actuator rotates the drive rod about the axis A-A to translate the knife to cut tissue disposed between the jaw members.

In one embodiment, a cam assembly is coupled to the distal end of the drive rod which includes a camming hub having a grooved outer periphery defined therein. The grooved outer periphery is configured to matingly engage a corresponding detent disposed on the knife wherein rotational movement of the drive rod correspondingly rotates the camming hub which, in turn, translates the detent and knife relative to the jaw members. The drive rod is slidingly received within the camming hub such that axial movement of the drive road does not reciprocate the knife.

The present disclosure also relates to an electrosurgical instrument for treating tissue which includes a housing having a shaft extending therefrom having an axis A-A defined therethrough. The shaft is at least partially flexible and includes first and second jaw members attached at a distal end thereof. Each jaw member includes an electrically conductive tissue contacting surface adapted to connect to a source of electrosurgical energy such that the electrically conductive tissue contacting surfaces are capable of conducting electrosurgical energy through tissue held therebetween. A drive assembly is disposed in the housing and has a first actuator operably coupled to a flexible drive rod for reciprocation thereof to move the jaw members from a first position in spaced relation to one another to a second position closer to one another for engaging tissue. A second actuator is disposed on the housing and is actuatable to articulate the shaft.

In one embodiment, the flexible portion of the shaft includes a plurality of joints nestingly arranged in series. Each joint may be configured to include one or more lumens defined therethrough for allowing reciprocation of the drive rod and articulation cables therein.

In one embodiment, the second actuator includes an articulation assembly having one or more user actuatable components (e.g., wheels) disposed on the housing which are operably coupled to a pulley system for reciprocating the articulation cables through the shaft. The articulation assembly may also include one or more guides for directing the pair of articulation cables into the pulley system and for pretensioning the articulation cables.

In another embodiment, the drive assembly includes a four bar mechanical linkage operably coupled to a drive rod wherein actuation of the four bar mechanical linkage reciprocates the drive rod which, in turn, moves the jaw members from a first position in spaced relation to one another to a second position closer to one another for engaging tissue.

In yet another embodiment, an adjustment actuator is coupled to the drive rod which allows a manufacturer to adjust the relative distance of the jaw members when disposed in the first position.

BRIEF DESCRIPTION OF THE DRAWINGS

Various embodiments of the subject instrument are described herein with reference to the drawings wherein.

DETAILED DESCRIPTION

The present disclosure relates to an electrosurgical forceps and more particularly, the present disclosure relates to an endoscopic electrosurgical forceps for sealing and/or cutting tissue utilizing an elongated, generally flexible and articulating shaft. In one embodiment, for example, such a device comprises a handle, handle assembly or other suitable actuating mechanism (e.g., robot, etc.) connected to a proximal end of a flexible, elongated body portion or shaft. A distal portion of the flexible shaft includes an articulating portion comprised of one or more joints to allow articulation of an end effector away from the longitudinal axis in response to actuation of articulation cables. An end effector is operatively supported on a distal end of the flexible shaft. The end effector includes a pair of jaws that can be actuated between a closed position and an open position. The jaws are adapted to supply electrical energy to tissue grasped between the jaws. The end effector also includes a knife assembly that can be actuated to cut tissue grasped within the jaws.

The functions of opening and closing the jaws; operating the knife assembly; and articulating the end effector can be performed remotely from the handle by actuation of various mechanisms in the handle. Mechanical motion may be transmitted from the handle through the flexible shaft to the end effector by flexible cables or rods within the flexible shaft. For example, in one embodiment two cables are used to provide articulation; one push-pull style cable opens and closes the jaws; and a second push-pull style cable actuates the knife assembly. The device is adapted to be placed in a lumen of a flexible endoscope and then inserted into a natural orifice of a patient and transited endoluminally through the anatomy of the natural lumen to a treatment site within or outside the natural lumen.

Figure 1:
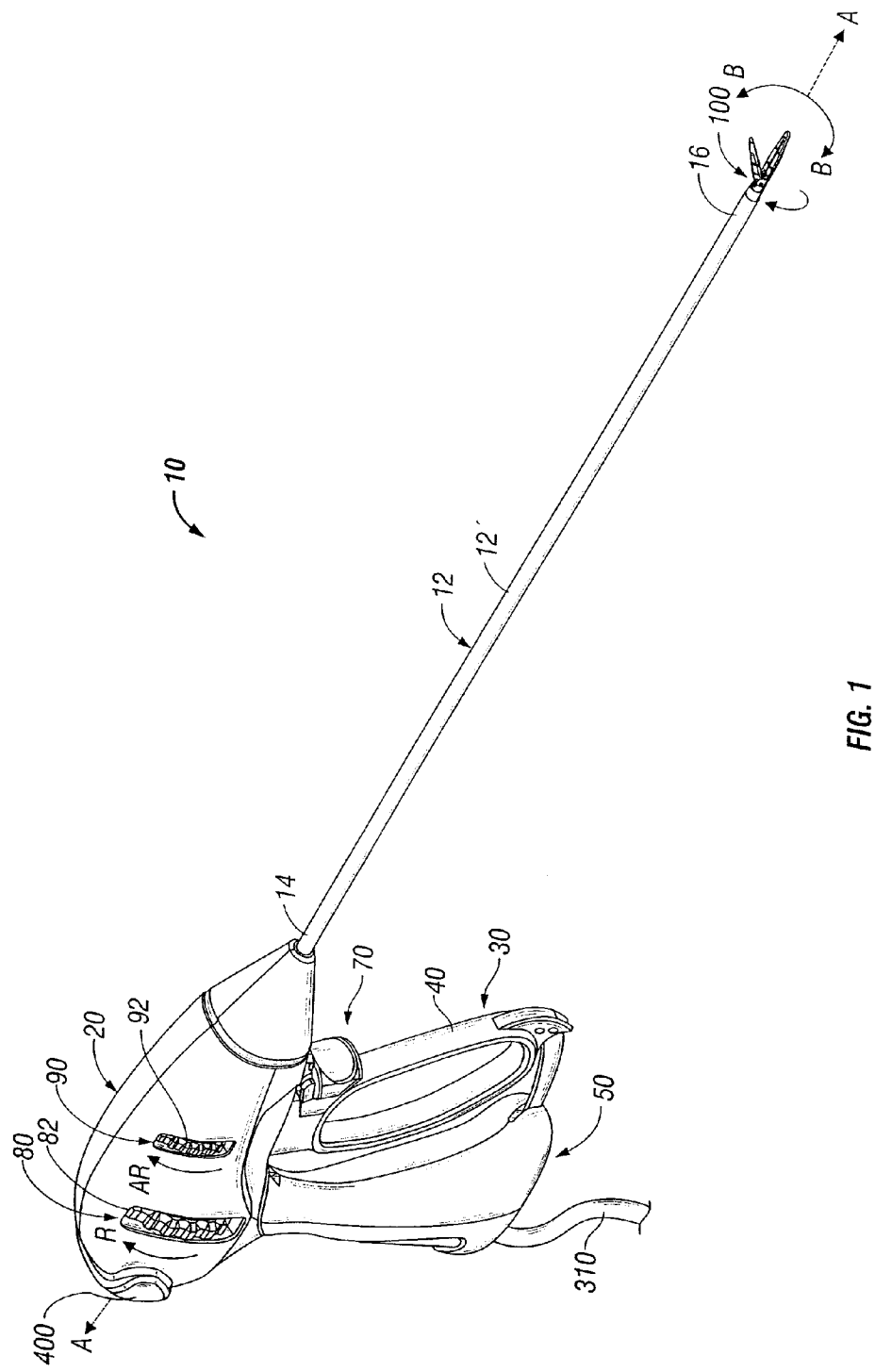
FIG. 1 is a perspective view of an endoscopic forceps showing a housing, a flexible shaft and an end effector assembly according to the present disclosure.
Figure 2:
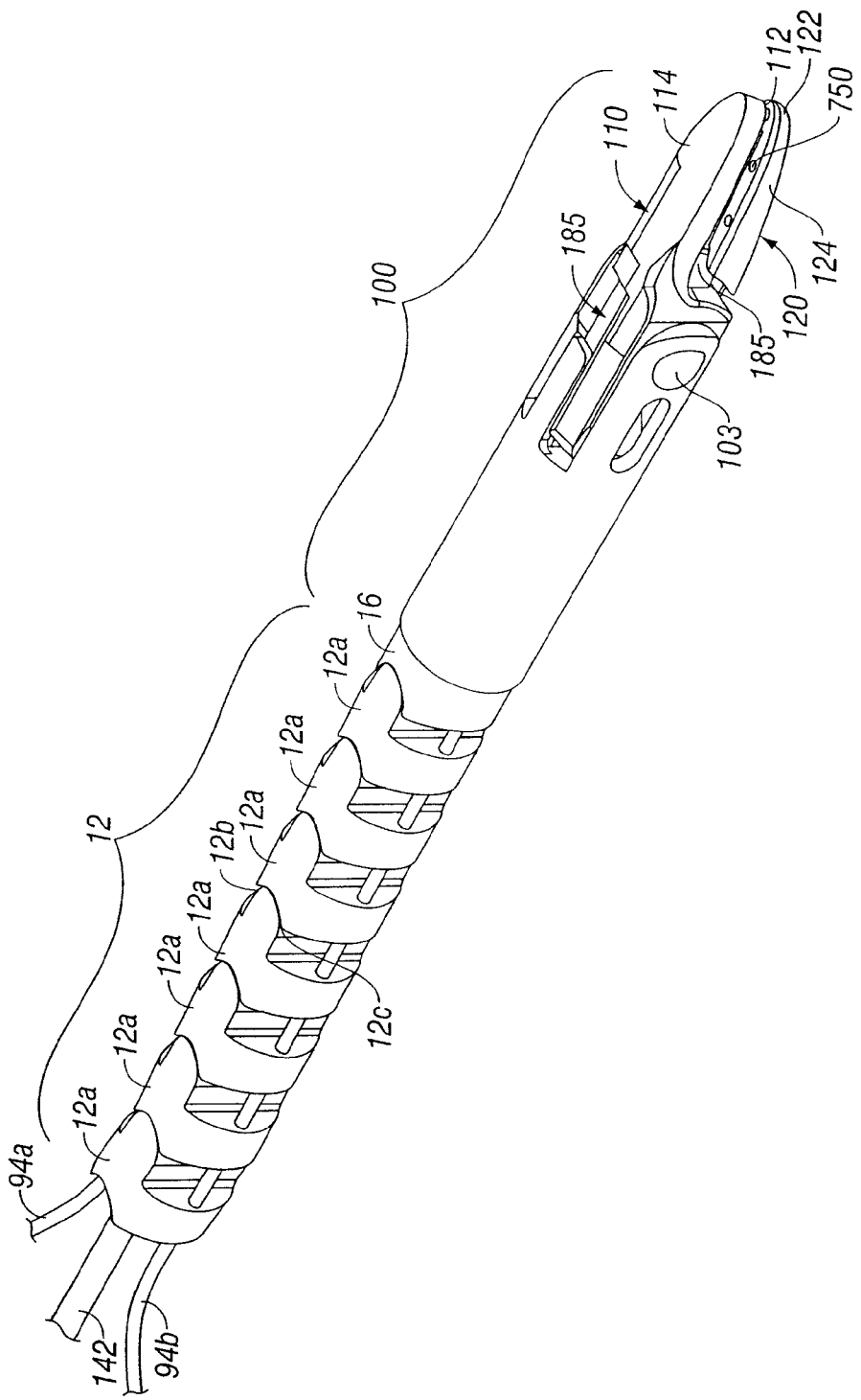
FIG. 2 is an enlarged front, perspective view of the flexible shaft (without an outer casing) and the end effector assembly of FIG. 1.
Figure 3:
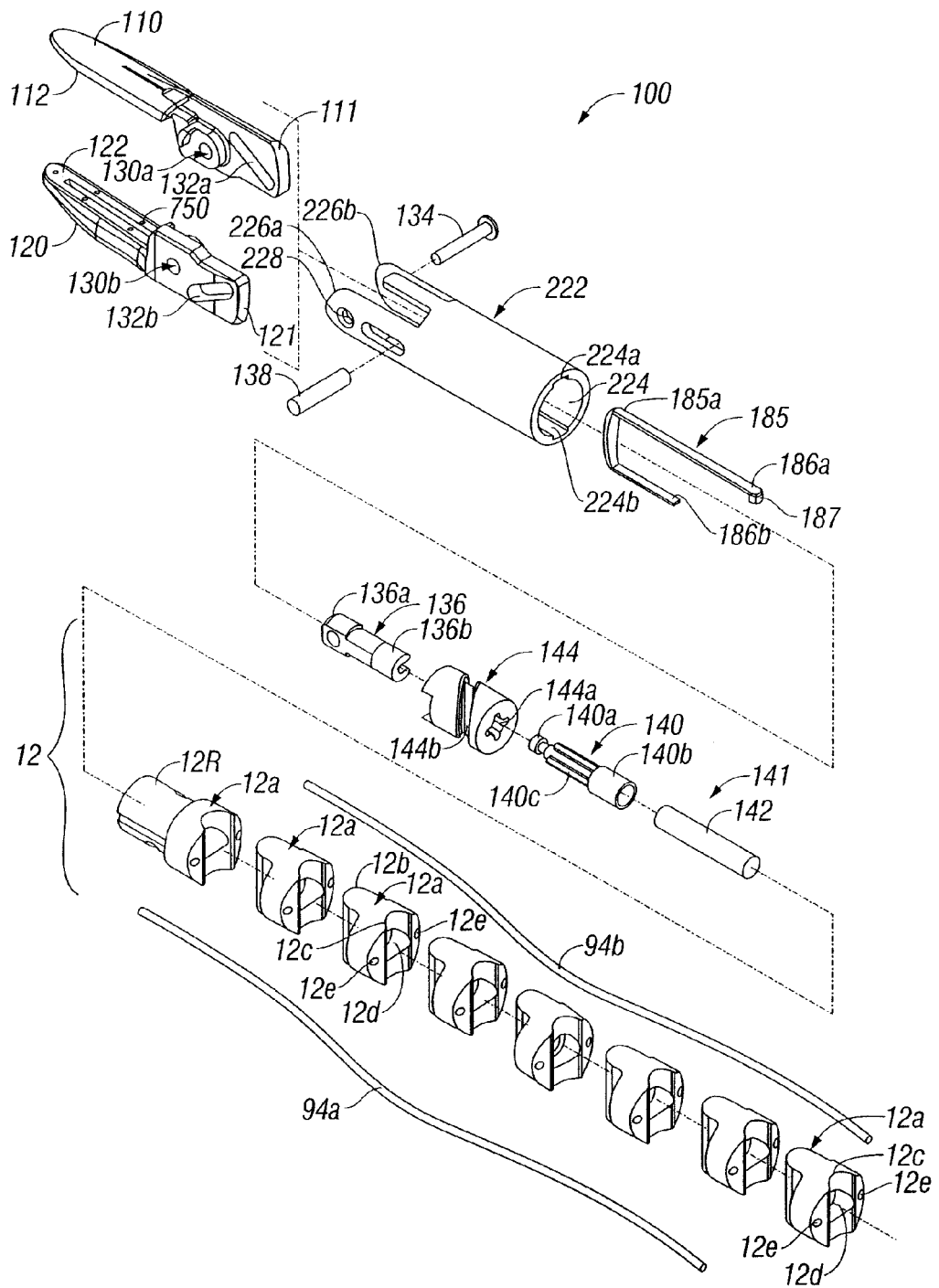
FIG. 3 is an enlarged rear, perspective view of the flexible shaft and end effector assembly with parts separated.

Turning now to FIGS. 1-3, one embodiment of an endoscopic vessel sealing forceps 10 is shown for use with various surgical procedures and generally includes a housing 20, a handle assembly 30, a rotating assembly 80, an articulation assembly 90, a trigger assembly 70 and an end effector assembly 100 which mutually cooperate to rotate, articulate, grasp, seal and divide tubular vessels and vascular tissue. Although the majority of the figure drawings depict a bipolar sealing forceps 10 for use in connection with endoscopic surgical procedures, the present disclosure may be used for monopolar surgical procedures which employ a remote patient pad for completing the current loop.

Forceps 10 includes a generally flexible shaft 12 which has a distal end 16 dimensioned to mechanically engage the end effector assembly 100 and a proximal end 14 which mechanically engages the housing 20. In one embodiment, the shaft 12 has at least two portions, a proximal portion and a distal portion. The proximal portion of the shaft may be formed of a flexible tubing (e.g., plastic) and may incorporate a tube of braided steel to provide axial (e.g., compressional) and rotational strength. The distal portion of shaft 12 may be also be flexible, but may incorporate one or more moving joints. A casing 12' may be employed to protect a plurality of internal moving joints 12a of the flexible shaft 12.

In one embodiment, the proximal portion of the shaft is flexible and non-articulating while the distal portion of shaft 12 is capable of articulating in response to movement of articulation cables or wires. Details of how the shaft 12 flexes are described in more detail below with respect to FIGS. 8 and 9. The proximal end 14 of shaft 12 is received within the housing 20 and connected to the rotating assembly 80, articulating assembly 90 and drive assembly 150. In the drawings and in the descriptions which follow, the term "proximal," as is traditional, will refer to the end of the forceps 10 which is closer to the user, while the term "distal" will refer to the end which is farther from the user.

As best seen in FIG. 1, forceps 10 also includes an electrosurgical cable 310 which connects the forceps 10 to a source of electrosurgical energy, e.g., a generator (not shown). It is contemplated that generators such as those sold by Valleylab—a division of Tyco Healthcare LP, located in Boulder, Colo. may be used as a source of electrosurgical energy, e.g., Valleylab's LIGASURE™ Vessel Sealing Generator and Valleylab's Force Triad™ Generator.

The generator may include various safety and performance features including isolated output, independent activation of accessories and/or so-called "Instant Response™" software which is a proprietary technology owned by Valleylab—a division of Tyco Healthcare LP. Instant Response™ is an advanced feedback system which senses changes in tissue 200 times per second and adjusts voltage and current to maintain appropriate power. The Instant Response™ technology is believed to provide one or more of the following benefits to vessel sealing: consistent clinical effect through all tissue types; reduced thermal spread and risk of collateral tissue damage; less need to "turn up the generator"; and designed for the minimally invasive environment.

Cable 310 is internally divided into cable lead 310a, 310b and 310c which each transmit electrosurgical energy through their respective feed paths through the forceps 10 to the end effector assembly 100 as explained in more detail below with respect to FIGS. 10 and 11.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 may be integrally associated with the housing 20 and is rotatable via rotating wheel 82 approximately 180 degrees in either direction about a longitudinal axis "A-A" defined through shaft 12. One envisioned rotating assembly 80 is disclosed in commonly-owned U.S. patent application Ser. No. 10/460,926. Another envisioned rotating assembly is disclosed in commonly-owned U.S. patent application Ser. No. 11/519,586. The entire contents of both applications are incorporated by reference herein.

Articulation assembly 90 may also be integrally associated with housing 20 and operable via wheel 92 to move the end effector assembly 100 in the direction of arrows "B-B" relative to axis "A-A". Wheel 92 may be provided in alternative arrangements such as disposed on the side of housing. Also, wheel 92 may be replaced by other mechanisms to actuate the articulation assembly 90 such as a levers, trackballs, joysticks, or the like. Details relating to the articulation assembly 90 are explained in more detail below with reference to FIGS. 8 and 9.

As mentioned above, end effector assembly 100 is attached at the distal end 16 of shaft 12 and includes a pair of opposing jaw members 110 and 120. Movable handle 40 of handle assembly 30 is ultimately connected to a drive assembly 150 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Turning now to the more detailed features of the present forceps housing 20, shaft 12 and end effector assembly 100, movable handle 40 is selectively movable about a pivot pin 29 from a first position relative to fixed handle 50 to a second position in closer proximity to the fixed handle 50 which, as explained below, imparts movement of the jaw members 110 and 120 relative to one another. The movable handle include a clevis 45 which forms a pair of upper flanges each having an aperture at an upper end thereof for receiving the pivot pin 29 therethrough. In turn, pin 29 mounts to opposing sides of the housing 20.

Clevis 45 also includes a force-actuating flange or drive flange (not shown) which aligns along longitudinal axis "A-A" and which abuts the drive assembly 150 such that pivotal movement of the handle 40 forces actuating flange against the drive assembly 150 which, in turn, closes the jaw members 110 and 120. A lower end of the movable handle 40 includes a flange 91 which is mounted to the movable handle 40 and which includes a t-shaped distal end 95 that rides within a predefined channel 51 disposed within fixed handle 50 to lock the movable handle 40 relative to the fixed handle 50.

The end effector assembly 100 includes opposing jaw members 110 and 120 which cooperate to effectively grasp tissue for sealing purposes. The end effector assembly 100 may be designed as a unilateral assembly, i.e., jaw member 120 is fixed relative to the shaft 12 and jaw member 110 pivots about a pivot pin 103 to grasp tissue or a bilateral assembly, i.e., both jaw members 110 and 120 move relative to axis "A-A". A drive rod 142 or drive sleeve is operably coupled to the drive assembly 150 and is selectively reciprocable via movement of handle 40 relative to handle 50 to actuate, i.e., pivot, the jaw members 110 and 120 relative to one another. In an embodiment of the device, drive rod 142 is flexible, and may be, for example, a cable.

In one particular embodiment according to the present disclosure and as best illustrated in FIGS. 1-3, a knife channel 115a and 115b may be defined in the upper and/or lower jaw member 110 and 120, respectively. The knife channel 115a and 115b is dimensioned to run through the center of the jaw members 110 and 120, respectively, such that a blade 185 may be selectively reciprocated to cut the tissue grasped between the jaw members 110 and 120 when the jaw members 110 and 120 are in a closed position. Blade 185 may be configured (or the blade 185 in combination with the end effector assembly 100 or drive assembly 150) such that the blade 185 may only be advanced through tissue when the jaw members 110 and 120 are closed thus preventing accidental or premature activation of the blade 185 through the tissue.

As best shown in FIGS. 2 and 3, jaw member 110 includes an insulative jaw housing 114 and an electrically conducive surface 112. Insulator 114 is dimensioned to securely engage the electrically conductive sealing surface 112 by stamping, by overmolding, by overmolding a stamped electrically conductive sealing plate and/or by overmolding a metal injection molded seal plate. All of these manufacturing techniques produce jaw member 110 having an electrically conductive surface 112 which is substantially surrounded by an insulative jaw housing 114. Jaw member 110 may also include one or more wire guides or channels (not shown) which are designed to guide cable lead 311 into electrical continuity with sealing surface 112.

Electrically conductive surface 112 and insulative jaw housing 114, when assembled, form a longitudinally-oriented slot 115a defined therethrough for reciprocation of the knife blade 185. It is envisioned that the knife channel 115a cooperates with a corresponding knife channel 115b defined in jaw member 120 to facilitate longitudinal extension of the knife blade 185 along a preferred cutting plane to effectively and accurately separate the tissue along the formed tissue seal.

Jaw member 120 includes similar elements to jaw member 110 such as an insulative jaw housing 124 and an electrically conductive sealing surface 122 which is dimensioned to securely engage the insulative jaw housing 124. Likewise, the electrically conductive surface 122 and the insulative jaw housing 124, when assembled, include a longitudinally-oriented channel 115a defined therethrough for reciprocation of the knife blade 185. As mentioned above, when the jaw members 110 and 120 are closed about tissue, knife channels 115a and 115b allow longitudinal extension of the knife 185 in a distal fashion to sever tissue along the tissue seal. A single knife channel, e.g., 115b, may be completely disposed in one of the two jaw members, e.g., jaw member 120, depending upon a particular purpose. Jaw member 120 may be assembled in a similar manner as described above with respect to jaw member 110.

Figure 7:
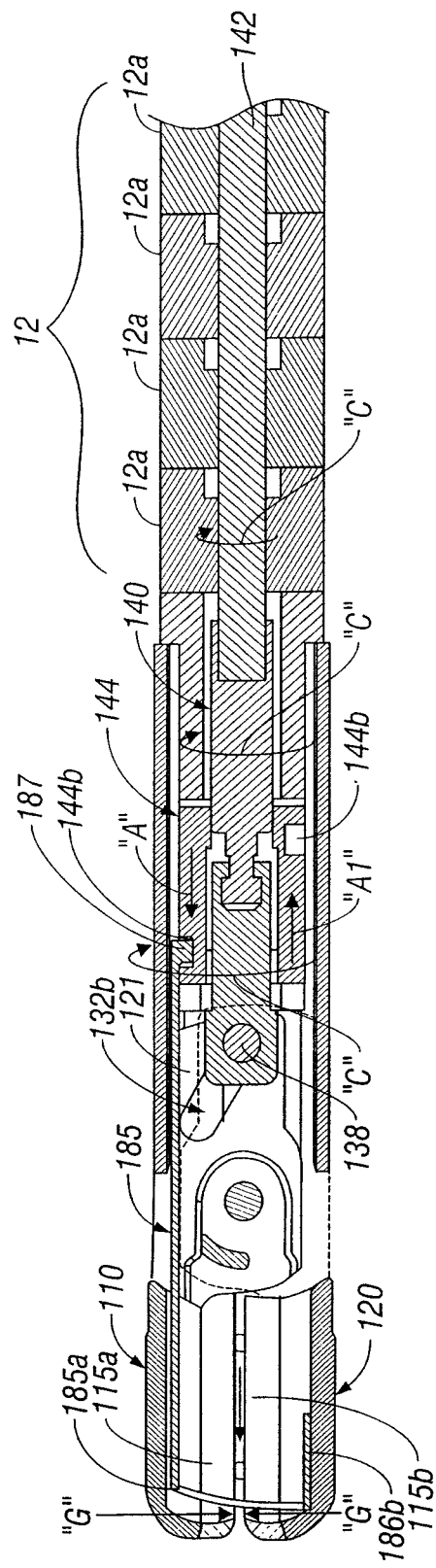
FIG. 7 is a side cross section of the flexible shaft and end effector of FIG. 2 showing distal translational movement of a cutting mechanism configured to cut tissue disposed within jaw members of the end effector assembly.

Jaw member 120 includes a series of stop members 750 disposed on the inner facing surfaces of the electrically conductive sealing surface 122 to facilitate gripping and manipulation of tissue and to define a gap "G" (see FIG. 7) between opposing jaw members 110 and 120 during sealing and cutting of tissue. The preferred gap "G" between the conductive sealing surfaces 112 and 122 to effectively and reliably seal tissue is between about 0.001 and about 0.006 inches. Stop members 750 may be employed on one or both jaw members 110 and 120 depending upon a particular purpose or to achieve a desired result. Stop members 750 may be thermally sprayed atop the electrically conductive sealing plate 122 or deposited or affixed in any other known fashion in the art. Moreover, the stop members 750 may be disposed in any configuration along the electrically conductive jaw surfaces 112 and 122 depending upon a particular jaw configuration or desired surgical result.

In one embodiment, jaw members 110 and 120 are engaged to the end of shaft 12 (or a sleeve (not shown) surrounding shaft 12) and are operable (via rotating assembly 80) to rotate about pivot 103 of the end effector assembly 100. Lead 311 carries a first electrical potential to jaw member 110 and a second electrical potential is transferred through drive rod 142 (or, alternatively, the above mentioned sleeve) to jaw member 120. Upon activation, the two electrical potentials transmit electrical energy through tissue held between conductive seal plates 112 and 122. Details relating to one envisioned electrical configuration of the lead 311 through forces 10 are discussed with reference to FIGS. 10 and 11 below.

Proximal movement of the drive rod 142 pivots the jaw members 110 and 120 to a closed position. More particularly, once actuated, handle 40 moves in a generally arcuate fashion towards fixed handle 50 about pivot pin 29 which forces clevis 45 to pull reciprocating drive rod 142 in a generally proximal direction to close the jaw members 110 and 120. Moreover, proximal rotation of the handle 40 causes the locking flange 71 to release, i.e., "unlock", the trigger assembly 70 for selective actuation of the knife 185.

The operating features and relative movements of the internal working components of one envisioned forceps 10, i.e., drive assembly 150, trigger assembly 70 and rotational assembly 80 are all described in commonly-owned U.S. patent application Ser. No. 10/460,926, the entire contents of which are incorporated herein.

Figure 4:
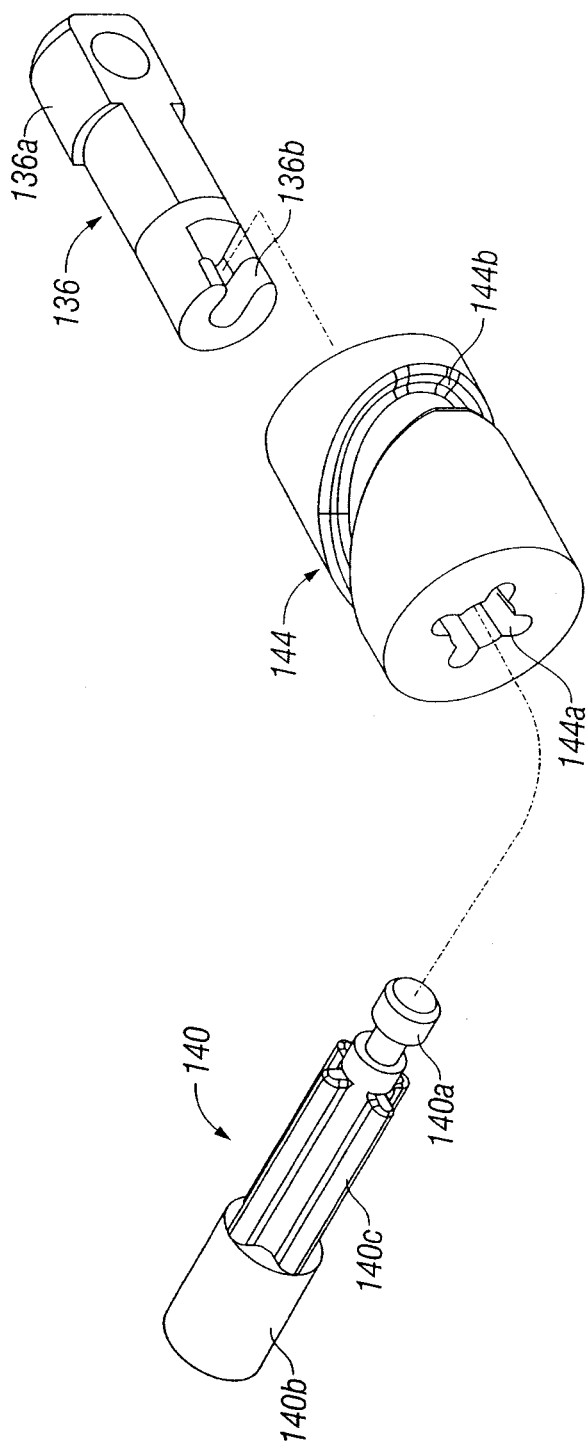
FIG. 4 is a greatly-enlarged perspective view of a cam mechanism of the end effector assembly.

As mentioned above, the jaw members 110 and 120 may be opened, closed, rotated and articulated to manipulate and grasp tissue until sealing is desired. This enables the user to position and re-position the forceps 10 prior to activation and sealing. As illustrated in FIG. 4, the end effector assembly 100 is rotatable about longitudinal axis "A-A" through rotation of the rotating knob 82 of rotating assembly 80. The end effector assembly 100 may also be articulated in either direction in the direction of arrows "B-B" as explained in more detail below with reference to FIGS. 8 and 9. Once the tissue is grasped (within the required pressure range of about 3 kg/cm$^2$ to about 16 kg/cm$^2$), the user then selectively applies electrosurgical energy to effectively seal tissue. Once sealed, the user then selectively advances the knife 185 by actuating the trigger assembly 70 to cut the tissue along the tissue seal.

The operating features and relative movements of one envisioned trigger assembly 70 are described in the above-mentioned commonly-owned U.S. patent application Ser. No. 10/460,926. In one embodiment, for example, actuation of the trigger assembly 70 causes a cable extending through shaft 12 and operatively coupled to knife 185 to move distally to thereby cut tissue along the tissue seal. In another embodiment, trigger assembly includes gearing that translates actuation of the trigger assembly to rotational motion of a cable extending through shaft 12.

One envisioned drive assembly 150 is also disclosed in U.S. patent application Ser. No. 10/460,926 which involves the selective reciprocation of a sleeve to open and close the jaw members 110 and 120. Another envisioned embodiment is described in U.S. application Ser. No. 11/519,586 wherein the drive assembly pulls a drive rod to open and close the jaw members 110 and 120.

With particular respect to FIGS. 2 and 3, the forceps 10 includes a plurality of joints 12a which are nestingly arranged in series to form flexible shaft 12. The distal end 16 of shaft 12 mechanically engages the end effector assembly 100 and the proximal end 14 of the shaft 12 mechanically engages the housing 20. Each of the plurality of joints 12a of the flexible shaft 12 includes a distal knuckle 12b and a proximal clevis 12c formed therewith. Each knuckle 12b operatively engages a clevis 12c of an adjacent joint 12a. Each joint 12a defines a central lumen 12d formed therein and a pair of opposed lumens 12e formed on either side of central lumen 12d. A pair of articulation cables 94a and 94b slideably extend through respective lumens 12e of joints 12. The operation of cables 94a and 94b is explained in further detail below with respect to FIGS. 8 and 9.

As seen in FIG. 3, end effector assembly 100 includes a jaw support member 222 which is configured to pivotably support jaw members 110 and 120. Jaw support member 222 defines a lumen 224 in a proximal end thereof and a pair of spaced apart arms 226a and 226b in a distal end thereof. Lumen 224 is configured and dimensioned to receive a stem 12f extending from a distal-most joint 12a of flexible shaft 12. Lumen 224 defines a pair of opposed channels 224a, 224b in a surface thereof which are configured to slidingly receive the knife blade 185 for reciprocation therein.

Jaws 110 and 120 are pivotably mounted on support member 222 by a jaw pivot pin 234 which extends through apertures 228 formed in arms 226a and 226b of support member 222 and respective pivot slots 132a, 132b formed in jaw members 110 and 120. To move jaws 110 and 120 between an open position and a closed position, an axially or longitudinally movable center rod 136 having a camming pin 138 is mounted within jaw support 222 at the center rod's 136 distal end 136a thereof. Camming pin 138 rides in and engages angled camming slots 132a and 132b formed in respective jaw members 110 and 120 such that axial or longitudinal movement of the center rod 136 via drive rod 142 causes jaws 110 and 120 to cam between open and closed positions.

End effector assembly 100 also includes a keyed rod 140 having a distal end 140a rotatably connected to a proximal end 136b of center rod 136. Keyed rod 140 includes a proximal end 140b fixedly connected to a distal end of drive rod 142, and a body portion 140c, disposed between distal end 140a and proximal end 140b, having a non-circular cross-sectional profile.

End effector assembly 100 further includes a camming assembly 141 including a camming hub 144 having a lumen 144a defined therethrough configured and adapted to slidably receive body portion 140c of keyed rod 140 therein. Camming hub 144 includes a mating mechanical interface defined therein which cooperates with the outer peripheral configuration of body portion 140c of keyed rod 140 to allow positive engagement of the two component halves for rotational purposes as explained in more detail below. The camming hub 144 also includes a helical or spiral groove 144b defined in an outer surface thereof which is configured to mechanically engage a detent 187 of the knife 185 the purpose of which is also explained in more detail below. Camming hub 144 is configured for rotatable disposition within lumen 124 of support member 222. In an alternative embodiment, camming hub 144 may be replaced by other mechanisms to translate rotational motion to linear motion (e.g., a lead screw, one or more gears, and the like).

Figure 5:
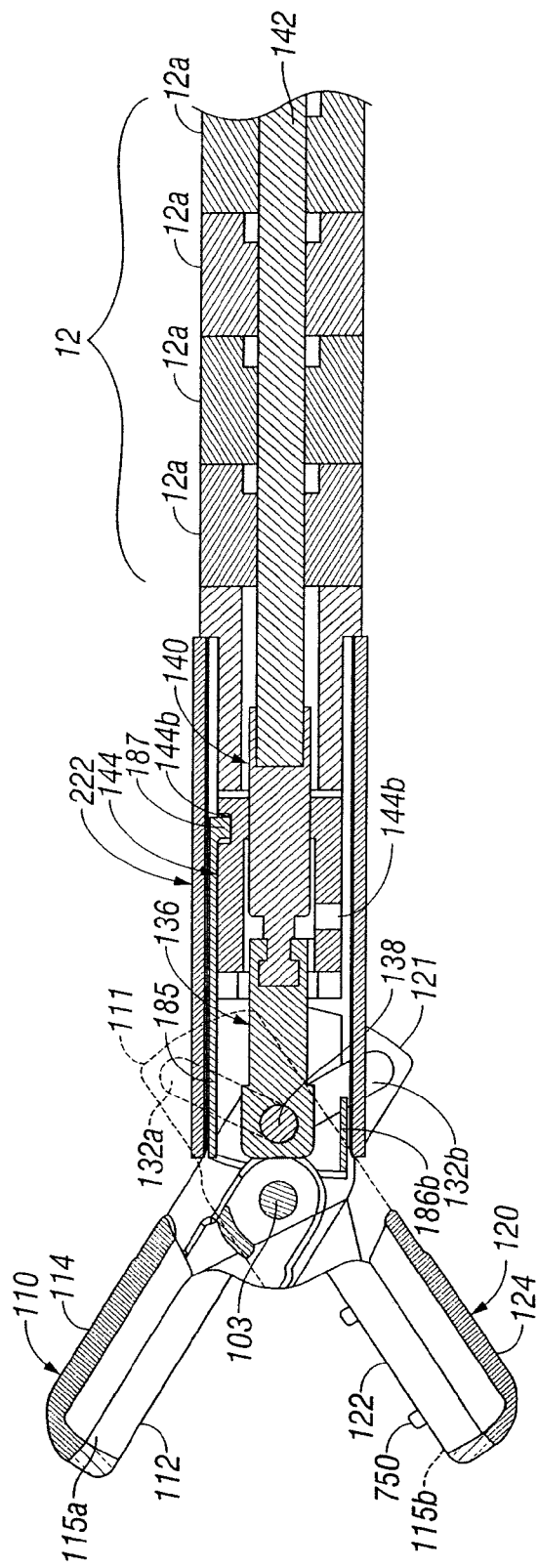
FIG. 5 is a side cross section of the flexible shaft and end effector assembly of FIG. 2 shown in an open configuration.
Figure 6:
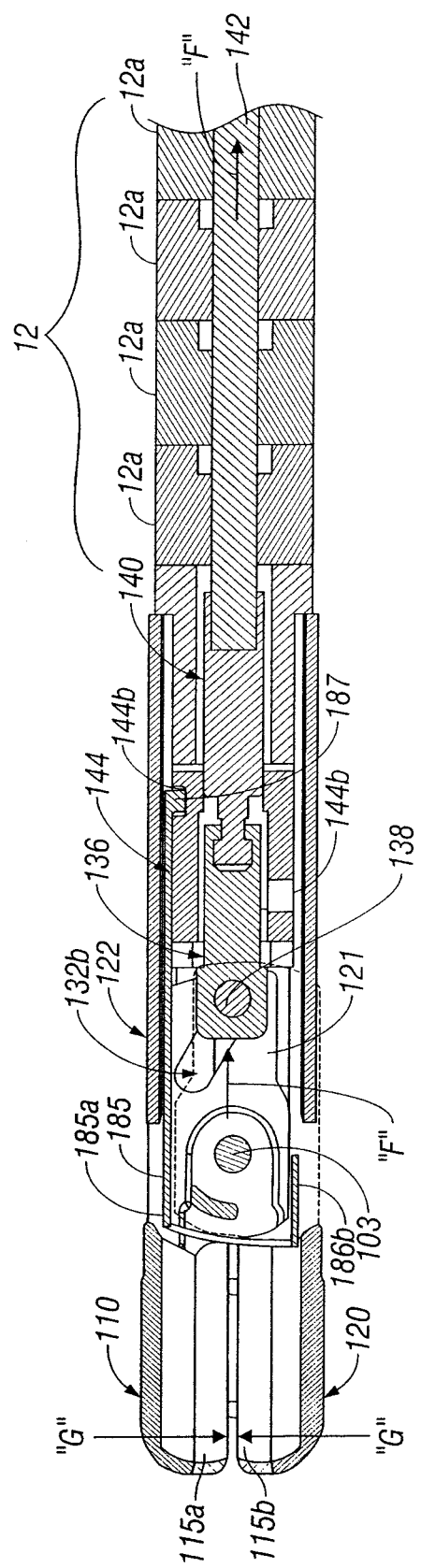
FIG. 6 is a side cross section of the flexible shaft and end effector assembly of FIG. 2 shown in a closed configuration.

In operation, the drive rod 142 is configured to provide two distinct and separate functions: axial displacement thereof actuates the jaw members 110 and 120 between the open to closed positions and rotational movement thereof advances the knife 185 through tissue. More particularly, axial displacement of drive rod 142 imparts axial displacement to keyed rod 140 which, in turn, imparts axial displacement to center rod 136. However, since camming hub 144 is axially slidably supported on keyed rod 140, no axial displacement is imparted thereto. As best shown in FIGS. 5 and 6, proximal translation of the drive rod 142 in the direction of arrow "F" forces camming pin 138 proximally within camming slots 132a and 132b to close the jaw members 110 and 120 about tissue with the requisite closure pressure and within the requisite gap "G" range. In an alternative embodiment (not shown), the functions actuated by drive rod 142 may be reversed with axial displacement advancing the knife 185 and rotational motion opening and closing jaw members 110 and 120. The electrically conductive sealing plates 112 and 122 are then energized to transmit electrical energy through tissue held between the jaw members 110 and 120.

One or more safety features may be employed either mechanically within the forceps 10 or electrically within the generator (not shown) to assure that tissue is effectively grasped between the jaw members 110 and 120 before energy is supplied.

Once a proper tissue seal is formed, the tissue may be severed along the tissue seal. Again, one or more safety features may be employed to assure that a proper seal has been formed prior to severing tissue. For example, the generator may include a safety lockout which electrically prevents or electro-mechanically prevents actuation of the knife 185 unless a proper and effective seal has been formed. As mentioned above, it is also important to note that vessel or tissue sealing is more than simply coagulating tissue and requires precise control of pressure, energy and gap "G" to effectively seal tissue.

The present disclosure incorporates a knife 185 which, when activated via the trigger assembly 70, progressively and selectively divides the tissue along an ideal tissue plane in precise manner to effectively and reliably divide the tissue into two sealed halves. The knife 185 allows the user to quickly separate the tissue immediately after sealing without substituting a cutting instrument through a cannula or trocar port. As can be appreciated, accurate sealing and dividing of tissue is accomplished with the same forceps 10.

It is envisioned that knife blade 185 may also be coupled to the same or an alternative electrosurgical energy source to facilitate separation of the tissue along the tissue seal. Moreover, it is envisioned that the angle of the knife blade tip 185a may be dimensioned to provide more or less aggressive cutting angles depending upon a particular purpose. For example, the knife blade 185 may be positioned at an angle which reduces "tissue wisps" associated with cutting. Moreover, the knife blade 185 may be designed having different blade geometries such as serrated, notched, perforated, hollow, concave, convex etc. depending upon a particular purpose or to achieve a particular result. It is envisioned that the knife 185 generally cuts in a progressive, uni-directional fashion (i.e., distally). As mentioned above, the drive rod performs two functions, opening and closing the jaw members 110 and 120 and advancing the knife 185 to sever tissue (see FIG. 7). In order to sever the tissue, rotation of drive rod 142 imparts rotation to keyed rod 140 which, in turn, imparts rotation to camming hub 144. However, since keyed rod 140 is rotatably connected to center rod 136, no rotation is imparted thereto.

End effector assembly 100 is operably coupled to a knife 185 which is slidably supported within respective channels 224a and 224b of support member 222. More particularly, knife 185 includes a sharpened or serrated edge 185a at a distal end thereof and a pair of guide flanges 186a and 186b which extend proximally therefrom. The proximal end of flange 186a includes a detent or protrusion 187 which is configured to engage and ride within spiral or helical groove 144b defined in camming hub 144.

In operation, as camming hub 144 is rotated in direction of arrow "C", proximal end 187 rides within groove 144b of camming hub 144 and moves in an axial direction "A1" relative thereto. Rotation of the camming hub 144 in one direction forces the blade 185 distally through knife channels 115a and 115b in jaw members 110 and 120, respectively, to sever tissue disposed therebetween. Rotation in the opposite direction forces proximal end 187 proximally to retract blade 185 to a proximal-most position. A spring may be operatively associated with the camming hub 144 to bias the knife 185 in a proximal-most orientation.

Figure 8:
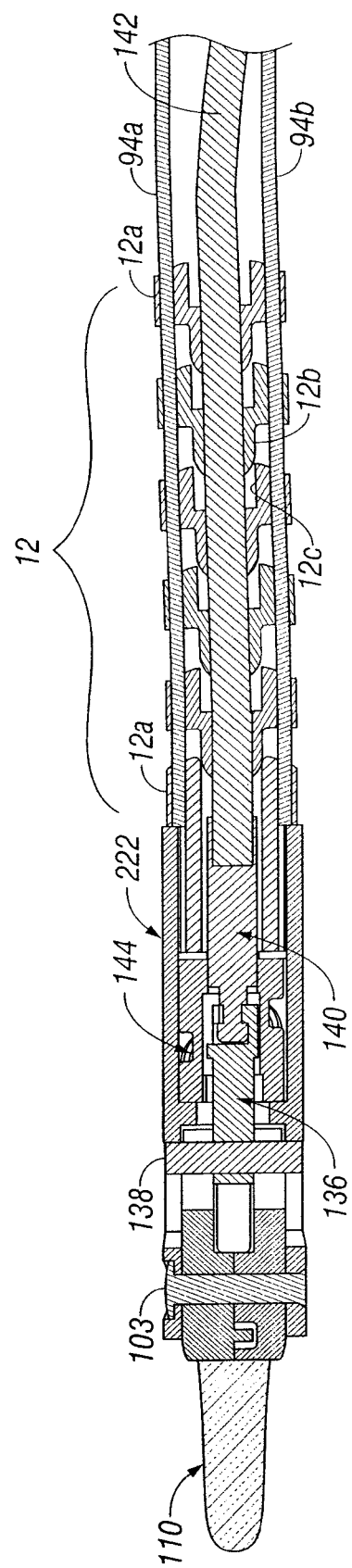
FIG. 8 is a longitudinal, cross-sectional view of the end effector assembly of FIG. 2 in an un-articulated condition.

As mentioned above, the end effector assembly 100 may also be selectively articulated. More particularly, as seen in FIG. 8 with end effector assembly 100 in an axially aligned condition, in order to articulate end effector assembly 100 via articulation assembly 90, wheel 92 is configured to rotate in a first direction to move end effector assembly 100 in a corresponding first direction and rotate in an opposite direction to move end effector assembly 100 in an opposite direction. Various pulley assemblies and gearing assemblies may be employed to accomplish this purpose.

For example, in one embodiment, the handle assembly may include at least one articulation cable operable from the housing. Each articulation cable includes a distal end operatively connectable with an end effector and a proximal end operatively connected to at least one of a control element, such as, for example, a slider, dial, lever, or the like, supported on the housing. In operation, movement of the control element results in movement of the at least one articulation cable, wherein movement of the at least one articulation cable in a first direction causes an articulation of the end effector and movement of the at least one articulation cable in a second direction results in articulation of the end effector in a second direction.

A pair of articulation cables may be provided each having a proximal end operatively connected to the control element such that movement of the control element in a first direction results in movement of a first articulation cable in a first direction and movement of a second articulation cable in a second direction; and movement of the control element in a second direction results in movement of the first articulation cable in the second direction and movement of the second articulation cable in the first direction.

Figure 9:
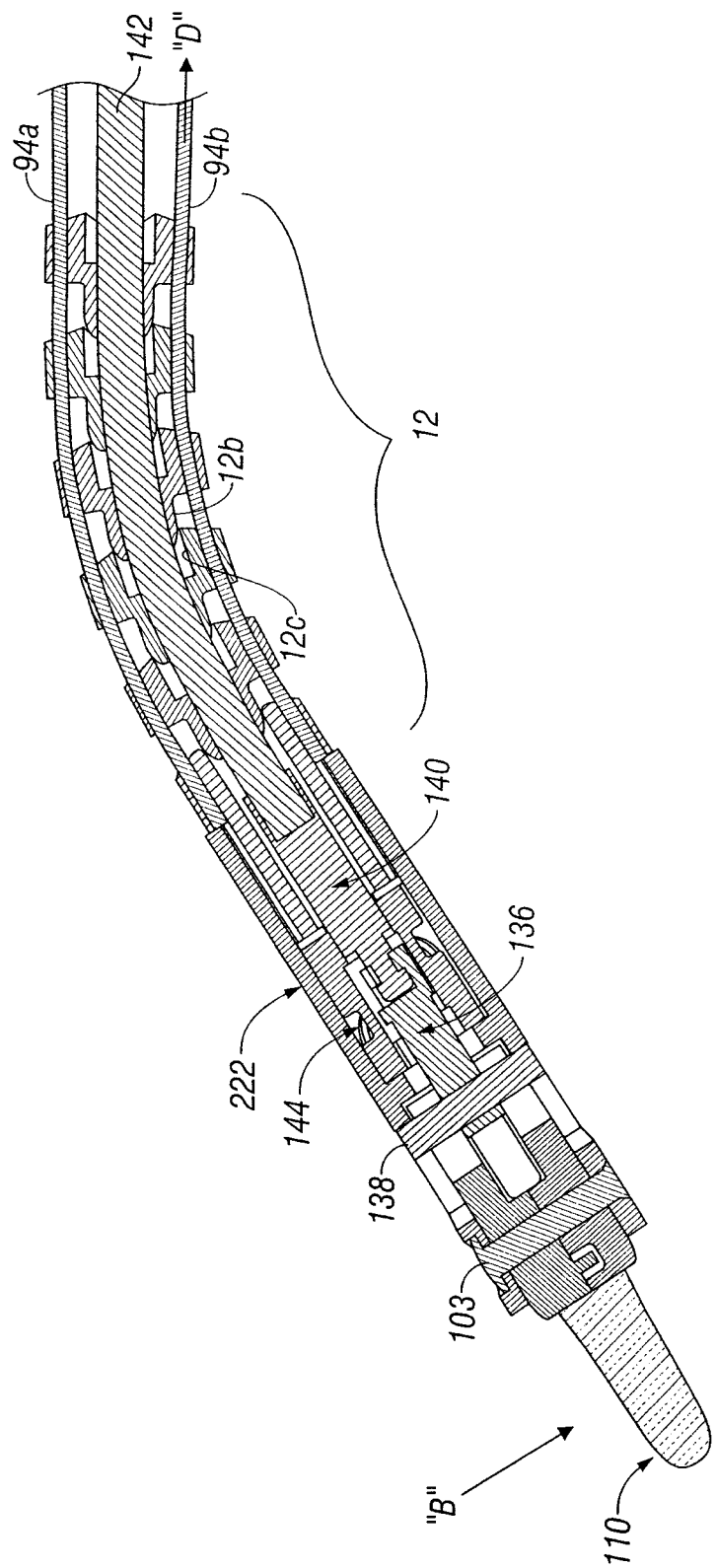
FIG. 9 is a longitudinal, cross-sectional view of the end effector assembly of FIG. 2 in an articulated condition.

More particularly and with reference to FIGS. 8 and 9, when first articulation 94b cable (i.e., the lower articulation cable as depicted in FIGS. 8 and 9) is withdrawn in a proximal direction via wheel 92, as indicated by arrow "D" of FIG. 9, a distal end of articulation cable 94b, anchored to a distal-most joint 12a, rotates about the interface between knuckles 112b and clevis' 112c thereby causing gaps defined therebetween, along a side surface thereof, to constrict. In so doing, end effector assembly 100 is articulated in a downward direction, in the direction of arrow "B", i.e., in a direction transverse to longitudinal axis "A-A". In order to return end effector assembly 100 to an un-articulated condition or to articulate end effector assembly 100 in an opposite direction, articulation cable 94a (i.e., the upper articulation cable as depicted in FIGS. 8 and 9) may be withdrawn in a proximal direction by rotation of wheel 92 in an opposite direction.

Various handles and/or handle assemblies may be operatively connected or otherwise associated with end effector assembly 100 in order to effect operation and movement of the various components thereof, i.e., drive cable 142 and/or articulation cables 94a, 94b. Exemplary handles and/or handle assemblies for use with end effector 1100 are disclosed in U.S. Provisional Application Ser. No. 60/849,562 filed on Oct. 5, 2006, entitled "PROGRAMMABLE HANDLE ASSEMBLY FOR SURGICAL DEVICES"; and U.S. Provisional Application Ser. No. 60/849,560 filed on Oct. 5, 2006, entitled "HANDLE ASSEMBLY FOR ARTICULATED ENDOSCOPIC INSTRUMENTS", the entire disclosures of each of which being incorporated herein by reference.

Figure 10:
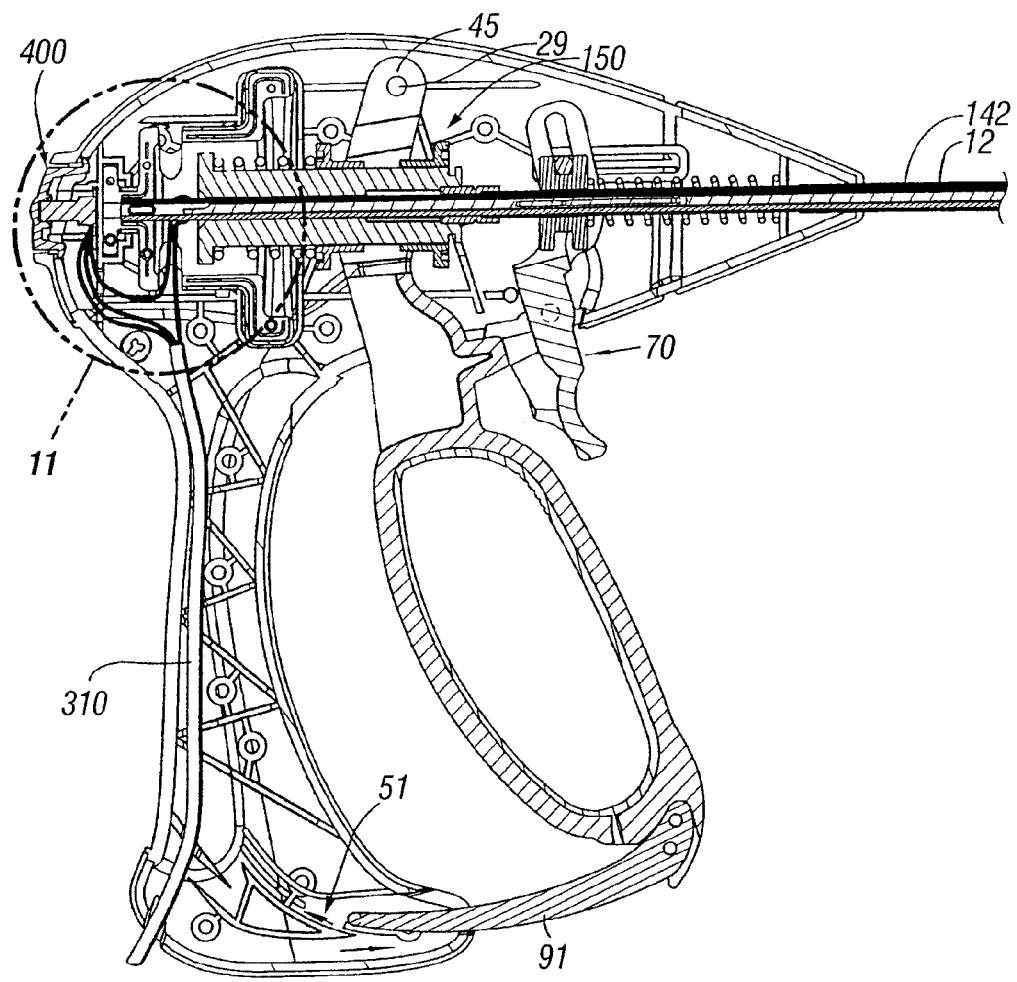
FIG. 10 is a cross-section of the housing showing the internal, electrical routing of an electrosurgical cable and electrical leads.
Figure 11:
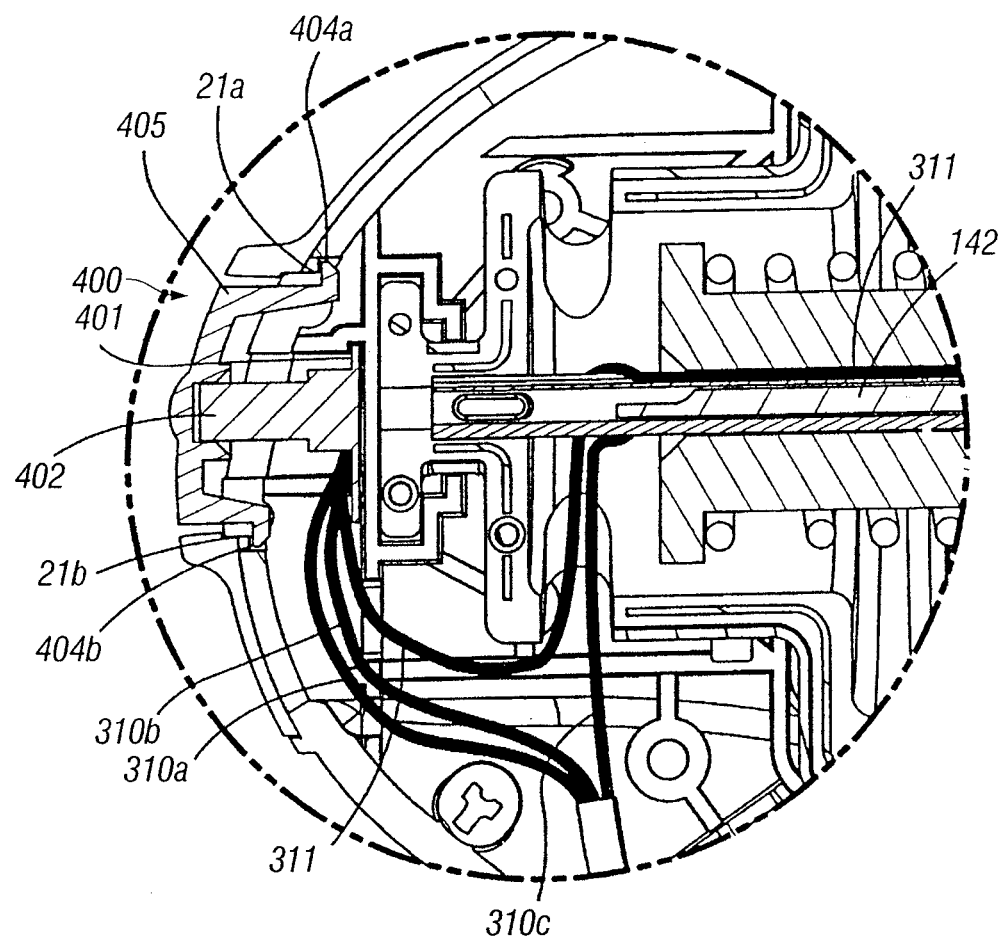
FIG. 11 is a greatly-enlarged view of the indicated area of detail of FIG. 10.
Figure 12:
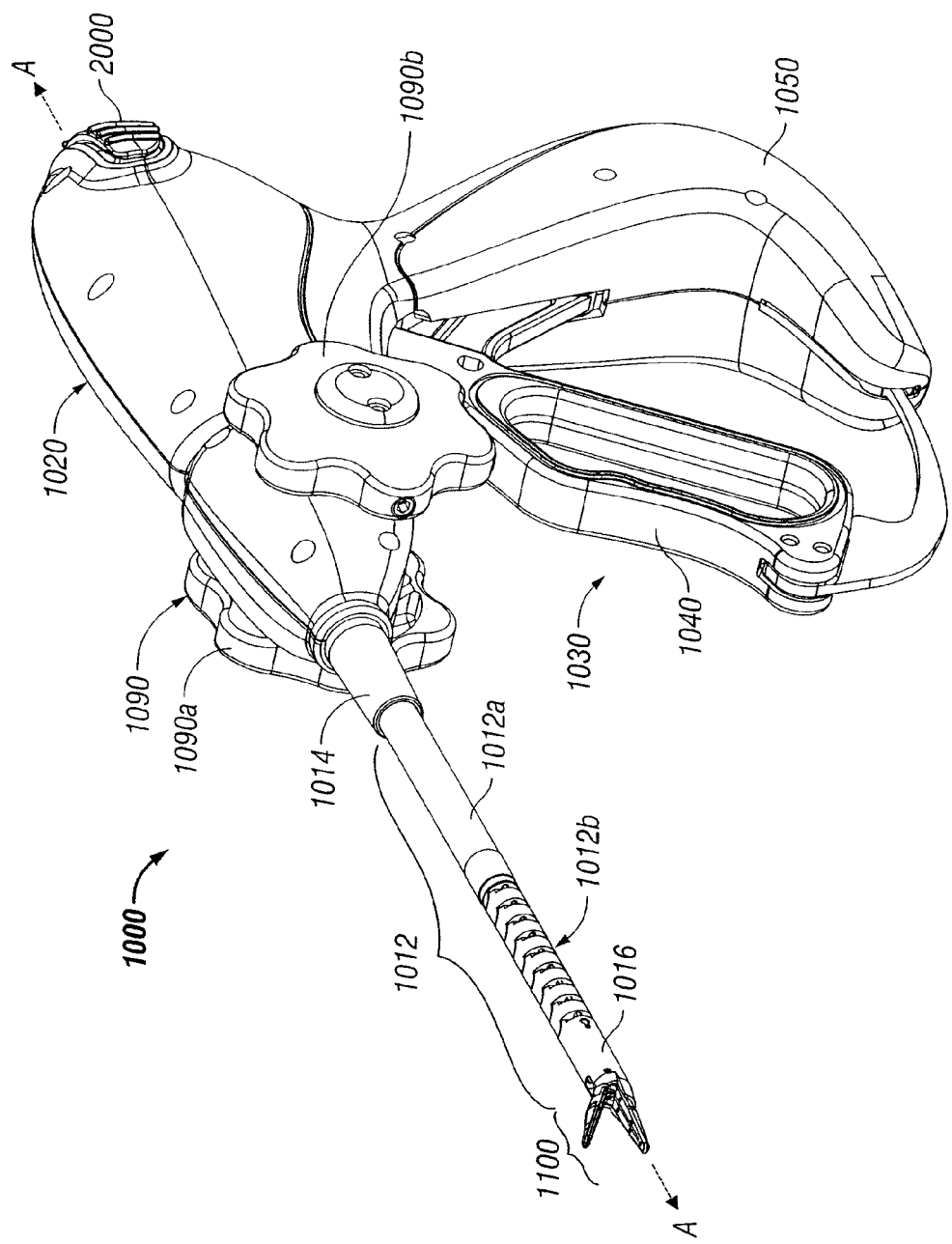
FIG. 12 is a perspective view of another embodiment of an endoscopic forceps showing a housing, a partially flexible shaft and an end effector assembly according to the present disclosure; of FIG. 12.
Figure 13:
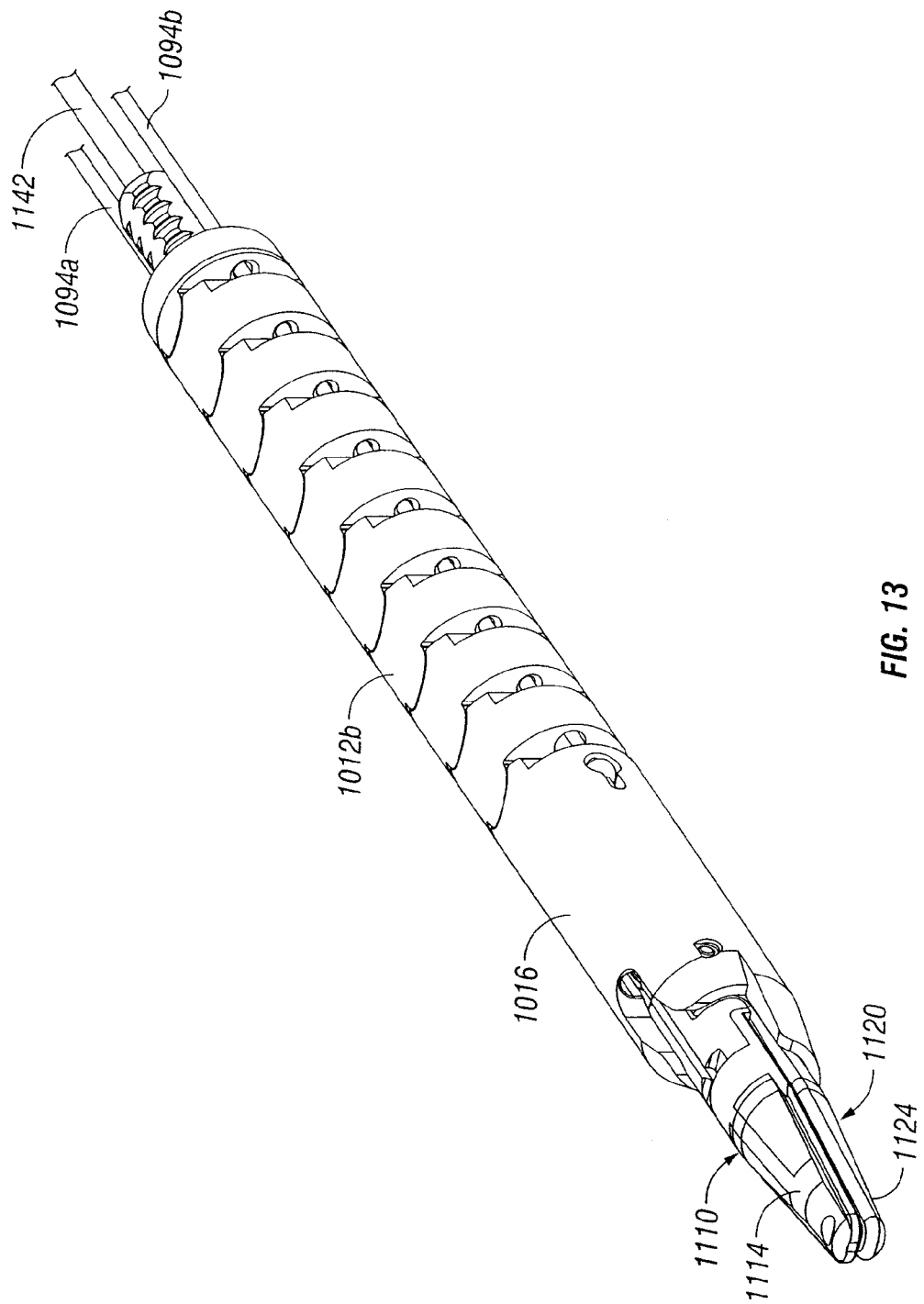
FIG. 13 is an enlarged perspective view of the partially flexible shaft

FIGS. 10 and 11 show one envisioned embodiment wherein the electrical leads 310a, 310b, 310c and 311 are fed through the housing 20 by electrosurgical cable 310. More particularly, the electrosurgical cable 310 is fed into the bottom of the housing 20 through fixed handle 50. Lead 310c extends directly from cable 310 into the rotating assembly 80 and connects (via a fused clip or spring clip or the like) to drive rod 142 to conduct the second electrical potential to jaw member 120. Leads 310a and 310b extend from cable 310 and connect to the hand switch or joy-stick-like toggle switch 400

In one embodiment, switch 400 may include an ergonomically dimensioned toggle plate 405 which may conform to the outer shape of housing 20 (once assembled). It is envisioned that the switch 400 permits the user to selectively activate the forceps 10 in a variety of different orientations, i.e., multi-oriented activation. As can be appreciated, this simplifies activation. A pair of prongs 404a and 404b extend distally and mate with a corresponding pair of mechanical interfaces 21a and 21b disposed within housing 20. Toggle plate 405 mechanically mates with a switch button 402 which, in turn, connects to an electrical interface 401. The electrical leads 310a and 310b are electrically connected to electrical interface 401. When the toggle plate 405 is depressed, trigger lead 311 carries the first electrical potential to jaw member 110. More particularly, lead 311 extends from interface 401 through the rotating assembly 80 and along a portion of shaft 12 to eventually connect to the jaw member 110. Lead 310c connects directly to either drive shaft 142 which ultimately connects to jaw member 120 or may be configured to extend directly to jaw member 120 to carry the second electrical potential.

It is envisioned that a safety switch or circuit (not shown) may be employed such that the switch cannot fire unless the jaw members 110 and 120 are closed and/or unless the jaw members 110 and 120 have tissue held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. U.S. patent application Ser. No. 10/427,832 describes one such feedback system, the entire contents of which being incorporated by reference herein.

As mentioned above, at least one jaw member, e.g., 120, may include a stop member 750 which limits the movement of the two opposing jaw members 110 and 120 relative to one another. In one embodiment, the stop member 750 extends from the sealing surface 122 a predetermined distance according to the specific material properties (e.g., compressive strength, thermal expansion, etc.) to yield a consistent and accurate gap distance "G" during sealing. It is envisioned for the gap distance between opposing sealing surfaces 112 and 122 during sealing ranges from about 0.001 inches to about 0.006 inches and, more preferably, between about 0.002 and about 0.003 inches. In one embodiment, the non-conductive stop members 750 are molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 750. Several thermal spraying techniques are contemplated which involve depositing a broad range of heat resistant and insulative materials on various surfaces to create stop members 750 for controlling the gap distance between electrically conductive surfaces 112 and 122.

FIGS. 15-21 show an alternate embodiment of an electrosurgical articulating forceps 1000 for use with vessel sealing procedures. May of the aforedescribed features of forceps 1000 are similar to forceps 10 and for the purposes of consistency, these features are hereby incorporated in the following discussion of forceps 1000 which is discussed below in a more abbreviated form.

Operation of forceps 1000 is similar to forceps 10 and includes movable handle 1040 which is movable relative to the fixed handle 1050. Movable handle 1040 is selectively moveable about a pair of pivots 1047 and 1057 (See FIG. 14C) from a first position relative to fixed handle 1050 to a second position in closer proximity to the fixed handle 1050 which, as explained below, imparts movement of the jaw members 1110 and 1120 relative to one another. In turn, each pivot 1047 and 1057 mounts to a respective housing half 1020a and 1020b.

Handle 1040 is operatively coupled to a pair of linkages 1042 and 1045 which upon movement of handle 1040 impart corresponding movement to the drive assembly 1700 as explained in more detail below. The arrangement of the handles 1040 and 1050, pivots 1047 and 1057 and linkages 1042 and 1045 provide a distinct mechanical advantage over conventional handle assemblies and allows the user to gain lever-like mechanical advantage to actuate the jaw members 1110 and 1120. This reduces the overall amount of mechanical force necessary to close the jaw members 1110 and 1120 to effect a tissue seal.

Much like the embodiment described with respect FIGS. 1-14, the lower end of the movable handle 1040 includes a flange 1044 which includes a t-shaped distal end 1044' that rides within a predefined channel 1051 disposed within fixed handle 1050. The t-shaped distal end 1044' lock the movable handle 1040 relative to the fixed handle 1050 and as explained in more detail below.

Figure 14A:
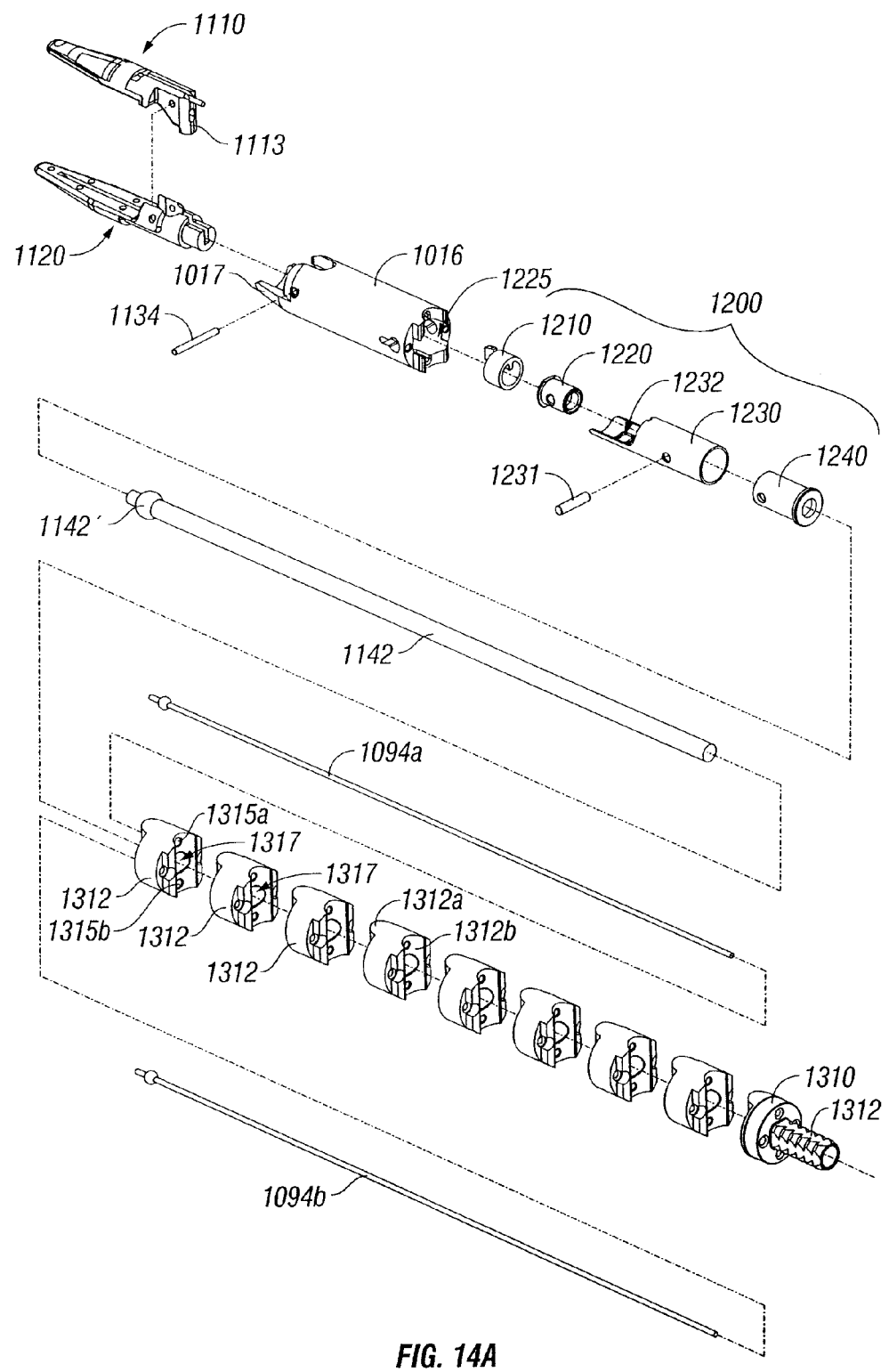
FIG. 14A is an enlarged, exploded perspective view of the partially flexible shaft of FIG. 13.

End effector assembly 1100 includes opposing jaw members 1110 and 1120 which cooperate to effectively grasp tissue for sealing purposes. The end effector assembly 1100 is designed as a unilateral assembly, i.e., jaw member 1120 is fixed relative to the shaft 1012 and jaw member 1110 pivots about a pivot pin 1134 to grasp tissue. More particularly, the unilateral end effector assembly 1100 includes one stationary or fixed jaw member 1120 mounted in fixed relation to the shaft 1012 and pivoting jaw member 1110 mounted about a pivot pin 1134 attached to the stationary jaw member 1120. A reciprocating sleeve 1230 is slidingly disposed within the shaft 1012 and is remotely operable by the drive assembly 1700. The pivoting jaw member 1110 includes a detent or protrusion 1113 which extends from jaw member 1110 through an aperture 1232 disposed within the reciprocating sleeve 1230 (FIG. 14A). The pivoting jaw member 1110 is actuated by sliding the sleeve 1230 axially within the shaft 1012 such that a distal end of the aperture 1232 abuts against the detent 1113 on the pivoting jaw member 1110 (See FIGS. 16A-17B). Pulling the sleeve 1230 proximally closes the jaw members 1110 and 1120 about tissue grasped therebetween and pushing the sleeve 1230 distally opens the jaw members 1110 and 1120 relative to one another for grasping purposes.

Unilateral end effector assembly 1100 may be structured such that electrical energy can be routed through the sleeve 1230 at the protrusion 1113 contact point with the sleeve 1230 or using a "brush" or lever (not shown) to contact the back of the moving jaw member 1110 when the jaw member 1110 closes. In this instance, the electrical energy would be routed through the protrusion 1113 to one of the jaw members 1110 or 1120. Alternatively, an electrical cable lead 1455 may be routed to energize one of the jaw members, e.g., jaw member 1120, and the other electrical potential may be conducted through the sleeve 1230 via electrical contact with lead 1450 (See FIG. 16C) and transferred to the pivoting jaw member 1110 which establishes electrical continuity upon retraction of the sleeve 1230.

Jaw members 1110 and 1120 include similar elements to jaw members 110 and 120 as described above such as jaw insulators 114 and 124 and electrically conductive sealing surfaces 112 and 122 (See FIG. 13), respectively. Jaw member 1120 also includes a series of stop members 750 (See FIG. 16B) disposed on the inner facing surface of electrically conductive sealing surface 1122 to facilitate gripping and manipulation of tissue and to define a gap "G" (See FIG. 17A) between opposing jaw members 1110 and 1120 during sealing and/or cutting of tissue. It is envisioned that the series of stop members 750 may be employed on one or both jaw members 1110 and 1120 in a variety of configurations depending upon a particular purpose or to achieve a desired result.

Figure 18A:
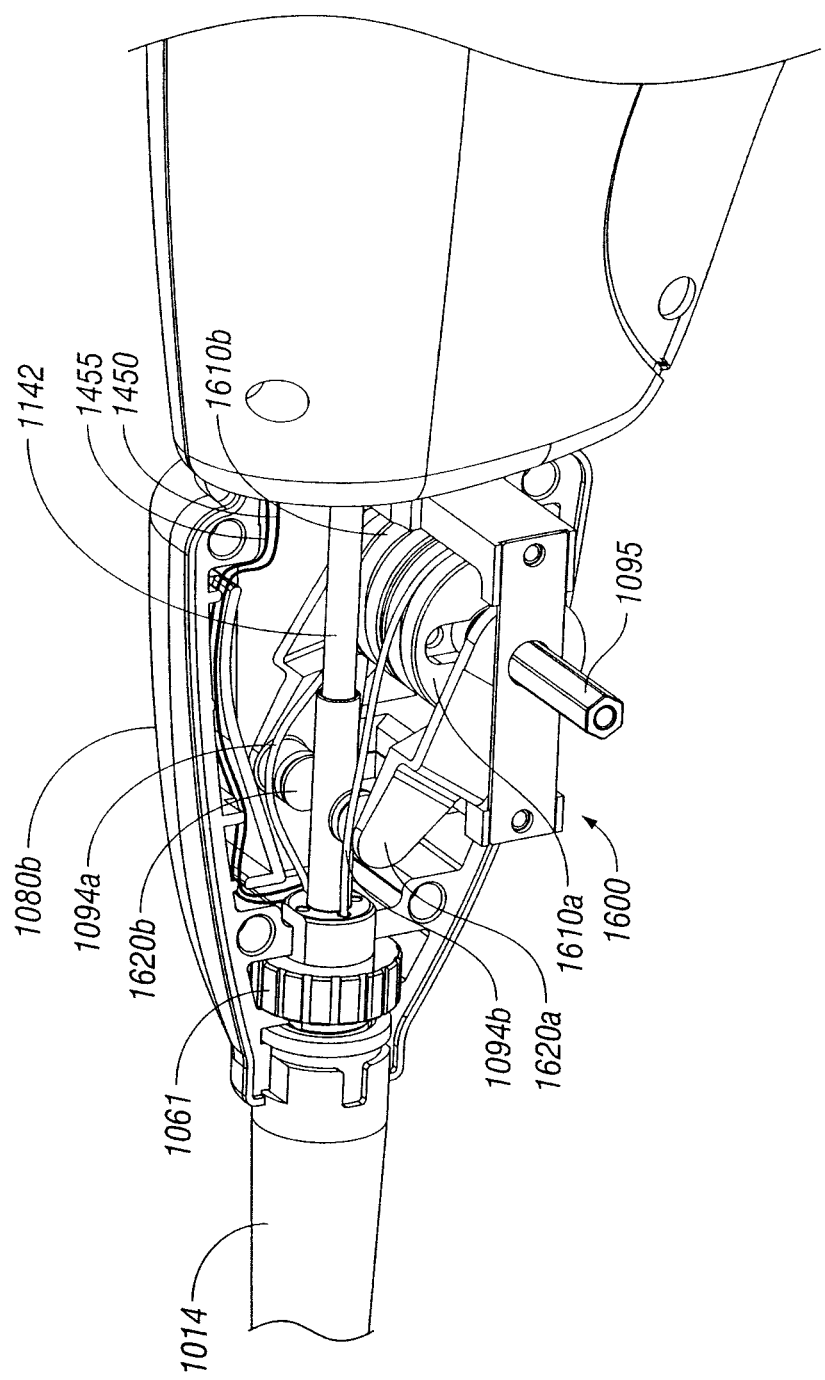
FIG. 18A is an enlarged internal perspective of an articulation assembly in accordance with the present disclosure.
Figure 18B:
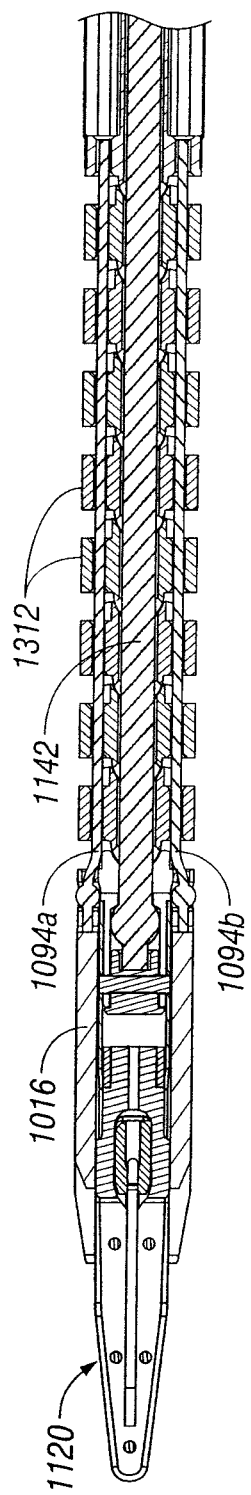
FIG. 18B is a top cross section of the partially flexible shaft of FIG. 13 in an aligned, non-articulated orientation.
Figure 18C:
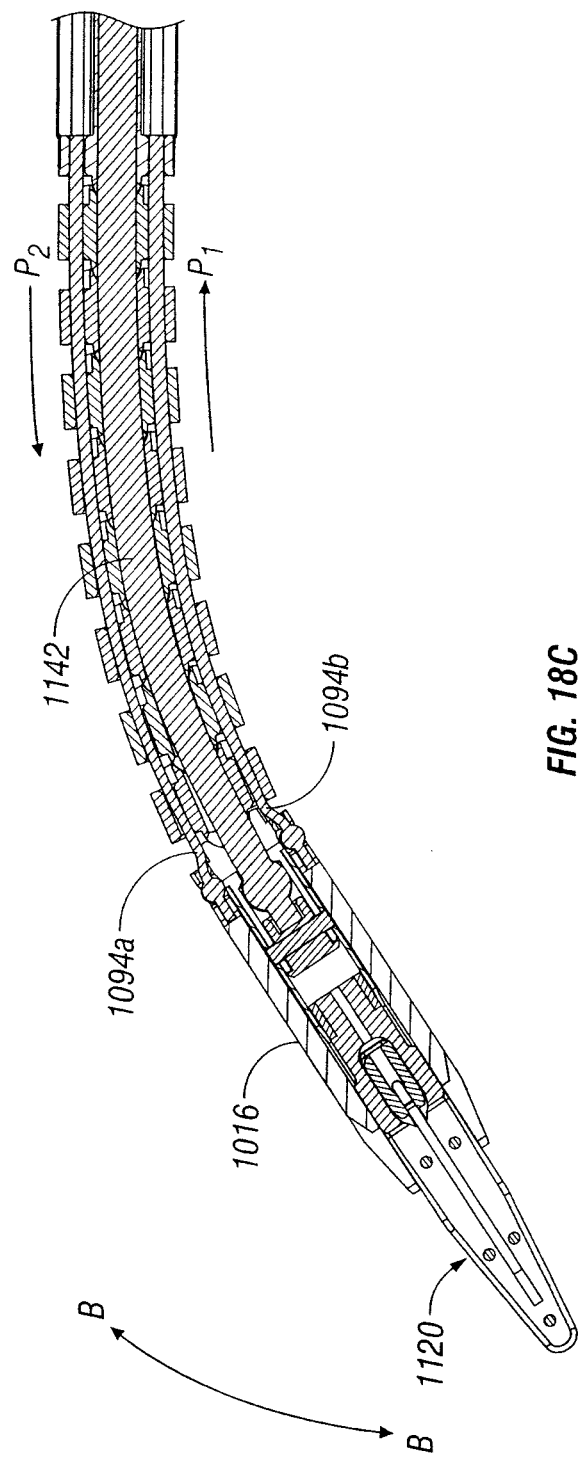
FIG. 18C is a top cross section of the partially flexible shaft of FIG. 13 in an articulated orientation.

Articulation assembly 1090 is operatively coupled to housing 1020. Articulation wheels 1090a and 1090b may be provided in alternative arrangements such as disposed on the side of housing 1020. It is envisioned that wheels 1090a and 1090b may be replaced by other mechanisms to actuate the articulation assembly 1090 such as a levers, trackballs, joysticks, or the like. More particularly, as seen in the comparison of FIGS. 18A-18C upon selective rotation of one the wheels 1090a, 1090b, the end effector assembly 1100 may be articulated from an axially aligned condition (FIG. 18B) to an articulated condition (FIG. 18C). In order to articulate end effector assembly 1100 via articulation assembly 1090, wheels 1090a and 1090b are configured to rotate in a first direction to move end effector assembly 1100 in a corresponding first direction and rotate in an opposite direction to move end effector assembly 1100 in an opposite direction. Various pulley assemblies and gearing assemblies may be employed to accomplish this purpose.

Figure 16A:
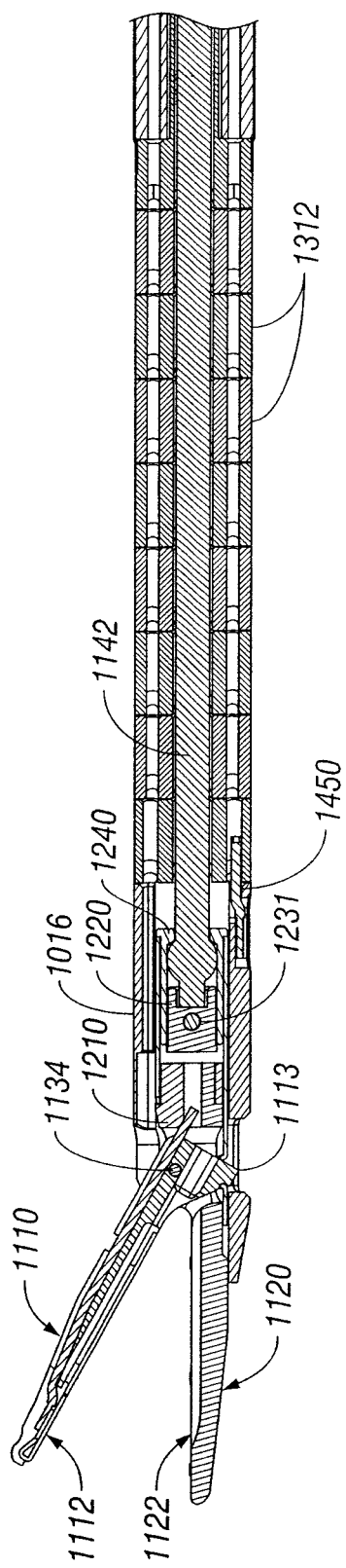
FIG. 16A is a side cross section of the partially flexible shaft of FIG. 13 with end effector assembly shown in open configuration.
Figure 16B:
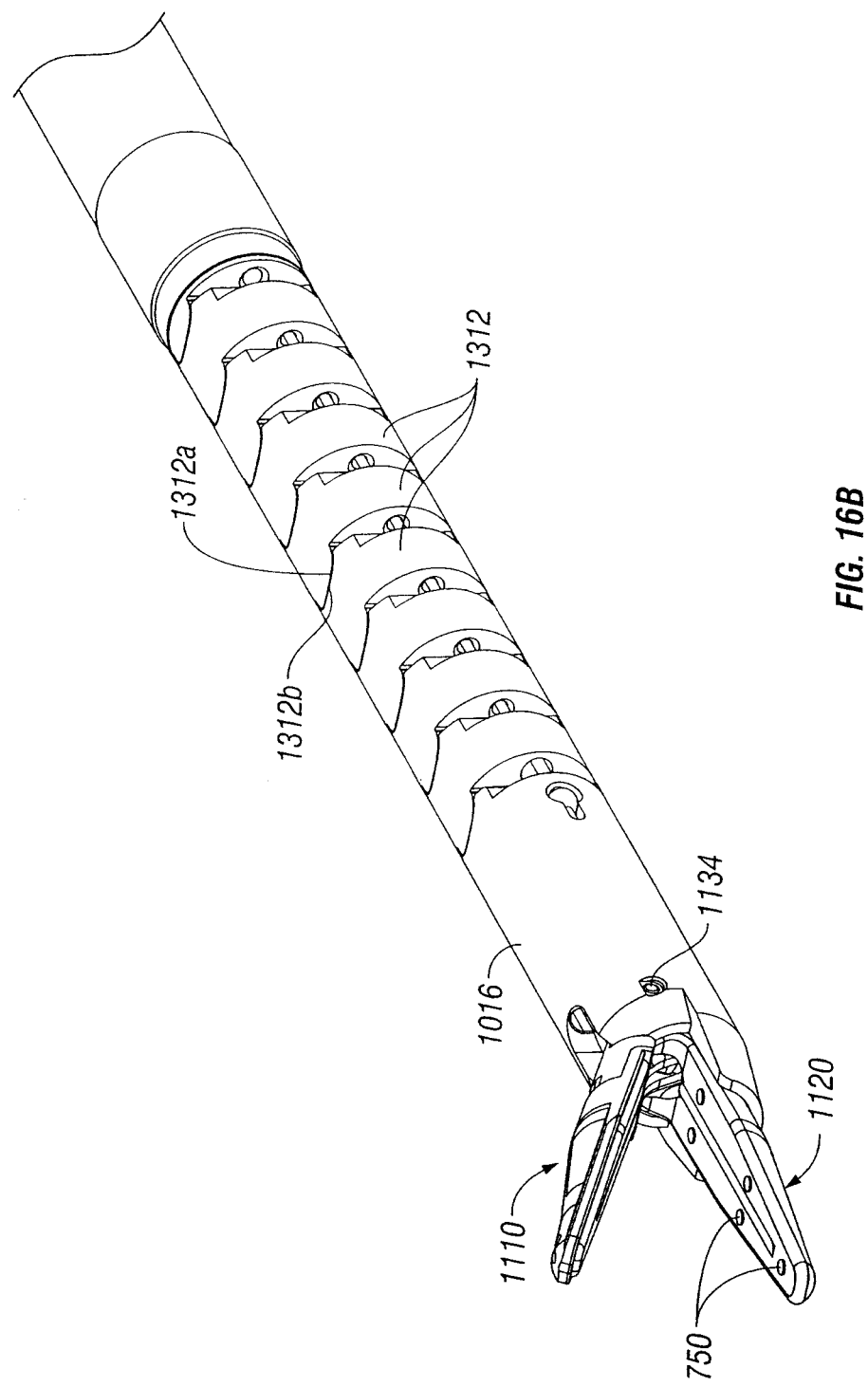
FIG. 16B is a front perspective of the partially flexible shaft of FIG. 13 with end effector assembly shown in open configuration.
Figure 16C:
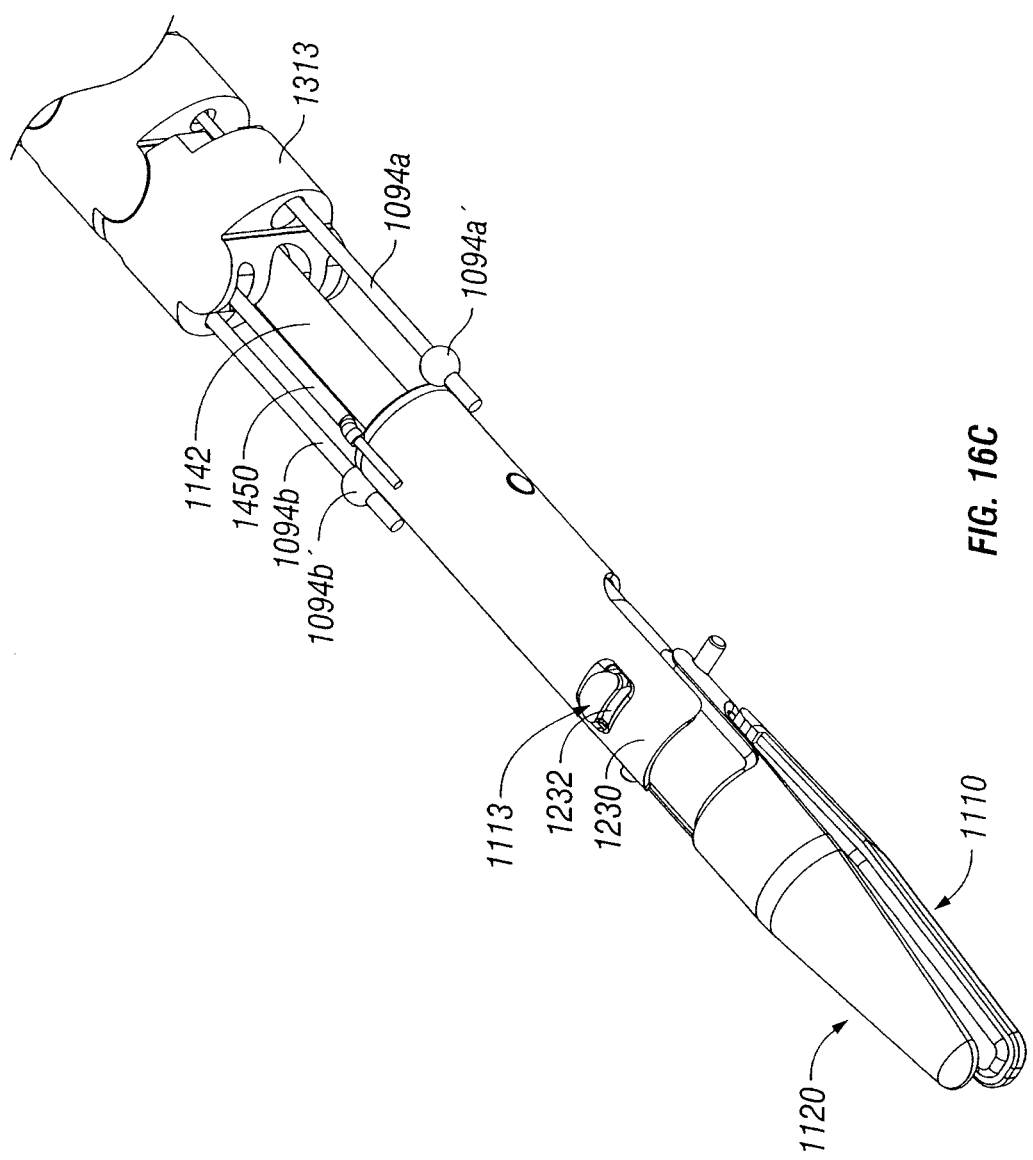
FIG. 16C is a bottom perspective of the partially flexible shaft of FIG. 13 with end effector assembly shown in partially open configuration.
Figure 17A:
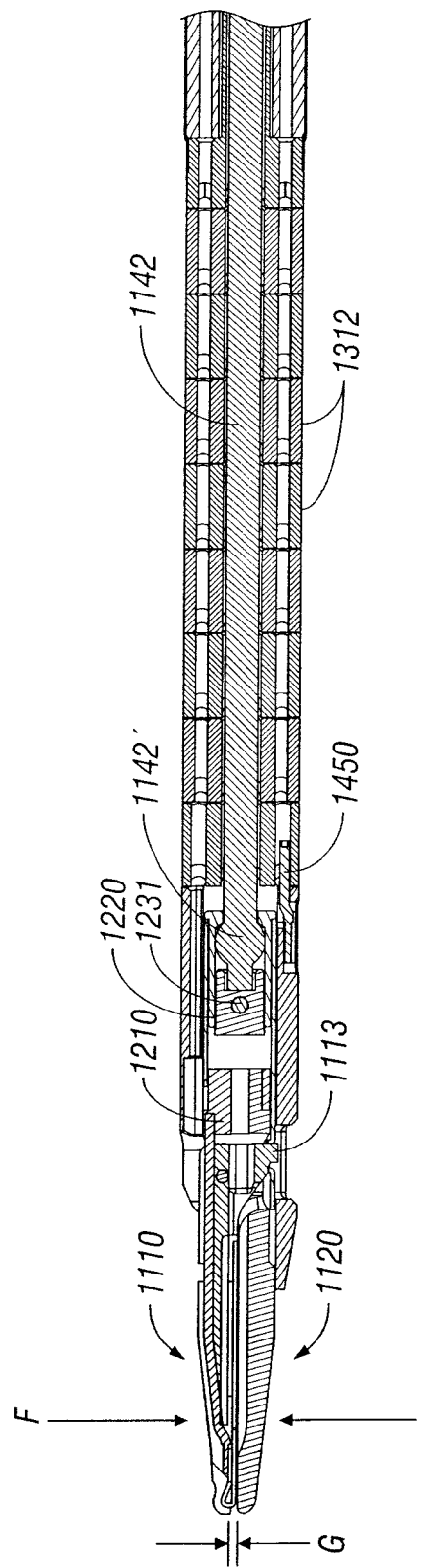
FIG. 17A is a side cross section of the partially flexible shaft of FIG. 13 with end effector assembly shown in closed configuration.
Figure 17B:
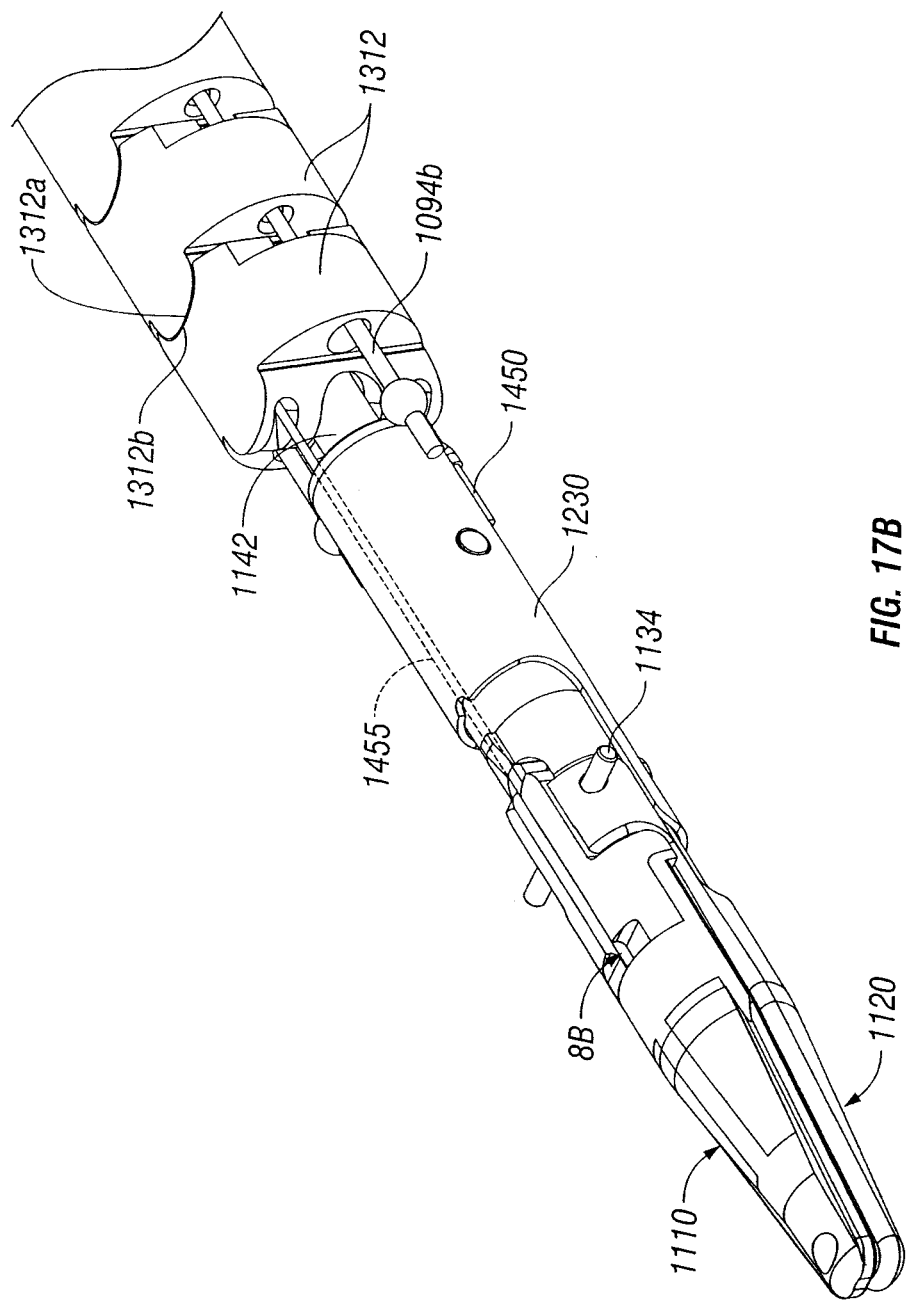
FIG. 17B is a front, internal perspective of the partially flexible shaft of FIG. 13 with end effector assembly shown in closed configuration.

For example and similar to the articulation arrangement described above, two articulation cables 1094a and 1094b may be utilized to articulate the flexible portion 1012b of shaft 1012. As best seen in FIG. 16C, each articulation cable 1094a and 1094b includes a distal end 1094a' and 1094b' which operatively connects with an end effector coupling assembly 1016 disposed at the distal end of shaft 1012. Coupling assembly 1016 includes a cavity 1225 defined therein configured to receive a series of mechanically inter-cooperating elements which are designed to engage the drive rod 1142 for reciprocation therein as well as guide the various electrical connections to the jaw members 1110 and 1120. The drive rod 1142 is preferably made from a flexible, friction-reducing material to allow the drive rod 1142 to bend in a given direction when the forceps 1000 is articulated. The friction-reducing material reduces buckling during articulation.

Coupling assembly includes a pair of bushings 1220 and 1240 which engage and secure a distal end 1142' of the drive rod 1142 to the drive sleeve 1230 via pin 1231. Bushing 1240 is slidingly engaged atop drive rod 1142 proximal to end 1142' and bushing 1220 is configured to engage bushing 1240 and secure end 1142' therebetween. Pin 1231 couples the secured bushings 1240 and 1220 and drive rod 1142 to drive sleeve 1230. The drive sleeve 1230 (and secured drive rod 1142) is received within cavity 1225 for sliding translation therein upon actuation of the drive assembly 1700 as explained in more detail below.

Coupling assembly 1016 also includes a locking element 1210 which is configured to engage a proximal end 1117 of jaw member 1120 to lock the coupling assembly 1016 (and drive rod 1142) in fixed relation relative to jaw member 1120 to limit any rotational movement therebetween. The coupling assembly 1016 also includes a distal flange 1017 which supports the lower jaw member 1120 once assembled (See FIG. 14A). As best shown in FIG. 16C, the coupling assembly 1016 also supports the electrical connection between lead 1450 and driving sleeve 1230. In addition, coupling assembly 1016 also guides electrical lead 1455 (shown in phantom) therethrough for connection to jaw member 1110.

In operation, movement of one of the articulation wheels 1090a and 1090b results in movement of the articulation cables 1094a and 1094b in opposite directions. More particularly, and as best shown in FIGS. 14C, 18A, 20A and 20B, the articulation assembly 1090 include wheels 1090a and 1090b which matingly couple to corresponding gear members 1096a and 1096b disposed on respective sides of housing 1020a and 1020b (See FIG. 20A). A hexagonal axle 1095 is mounted through both gear members 1096a and 1096b and capped on either end by wheels 1090a and 1090b. The axle 1095 is secured within the gear members 1096a and 1096b by mechanically mating surfaces (friction fit, geometric fit, etc.) or in other ways customary in the trade. The gear-like arrangement of the wheels 1090a and 1090b allow for incremental indexing of the articulation member 1090 in a given direction and a pair of set springs 1091 on each wheel prevent recoil of the wheel in any given direction. In other words, the set springs 1091 are configured to intermesh with the gears, e.g., gear 1096b, and allow incremental advancement in a clockwise or counter-clockwise direction. The biasing force of the set springs 1091 against the gear, e.g., gear 1096b, is sufficient to maintain the flexible shaft 1012b in any desired articulated position.

Axle 1095 supports pulley assembly 1600 within housing 1020 in operative association with cables 1094a and 1094b. More particularly, pulley assembly 1600 includes two pulleys 1610a and 1610b mounted for rotation atop axle 1095. Each pulley 1610a and 1610b includes a corresponding guide sleeve 1620a and 1620b which guide the respective cable 1094a and 1094b atop the corresponding pulley 1610a and 1610b to facilitate reciprocation thereof. As best shown in FIG. 18A, cable 1094a is designed to engage pulley 1620b for rotation one direction, while cable 1094b is designed to engage pulley 1620a for rotation in the opposite direction. As can be appreciated, this enables the pulleys 1610a and 1610b to operate in a push—pull manner to articulate the flexible shaft 1012b. In other words, as one cable 1094a is being pulled in the direction of P1, the other cable 1094b is being pushed (or relaxed) in the direction of P2 to allow the flexible shaft 1012b to articulate in a given direction (See FIG. 18C). The guide sleeves 1620a and 1620b also pre-tension the respective cables 1094b and 1094a to facilitate and enhance consistent articulation of the flexible shaft 1012b.

Figure 14B:
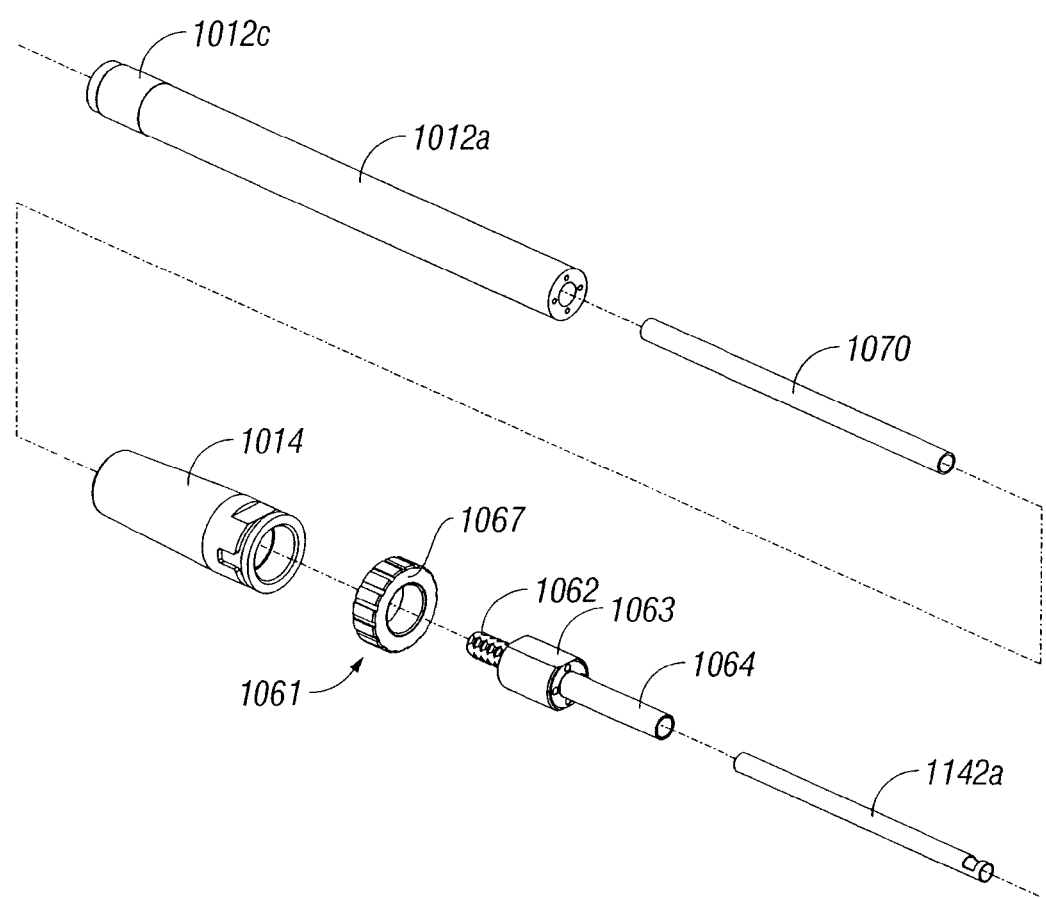
FIG. 14B is a greatly enlarged perspective view of a fine adjustment mechanism of according to the present disclosure.
Figure 14C:
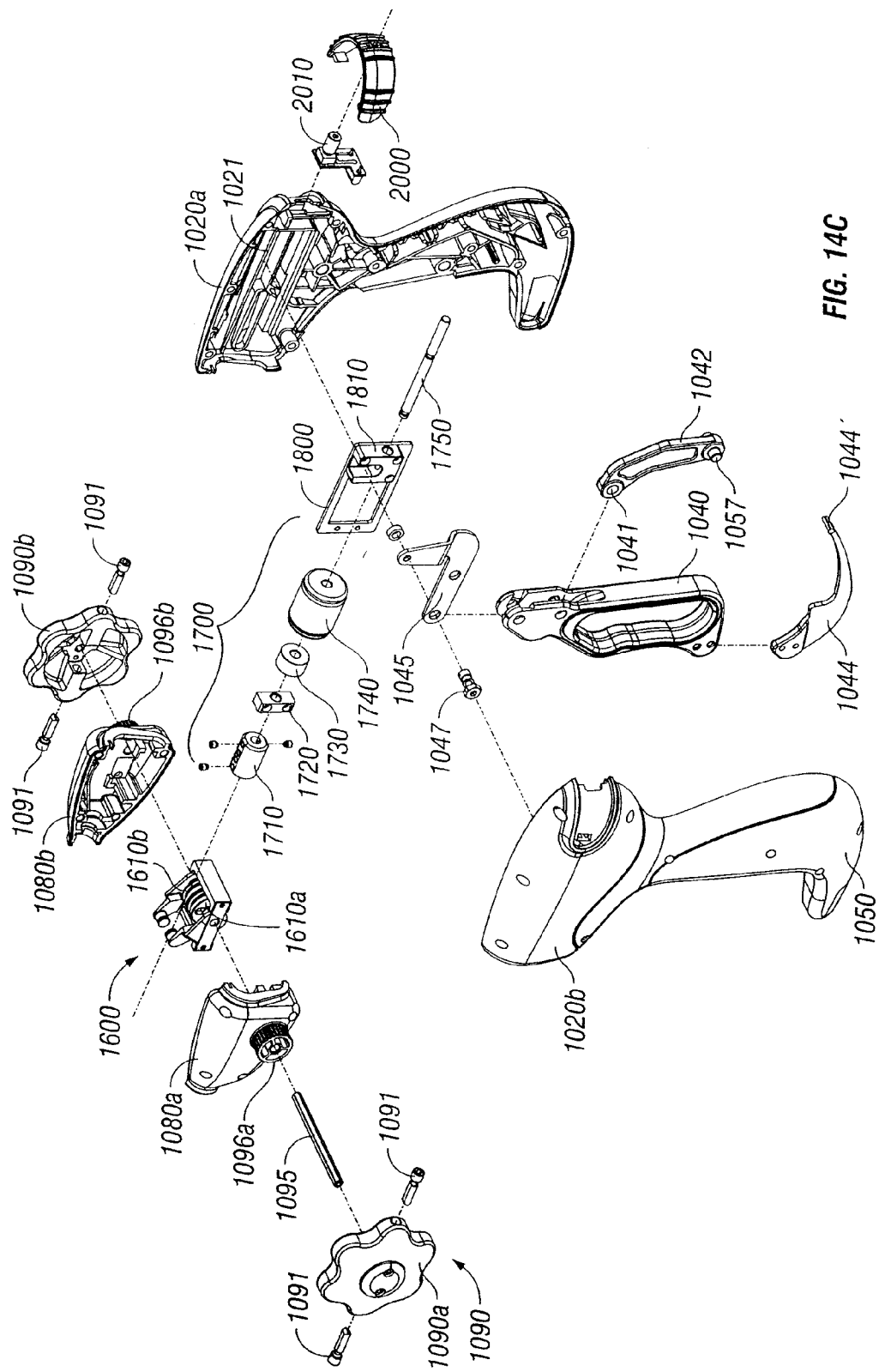
FIG. 14C is an exploded perspective view of the housing of the forceps of FIG. 12.
Figure 15A:
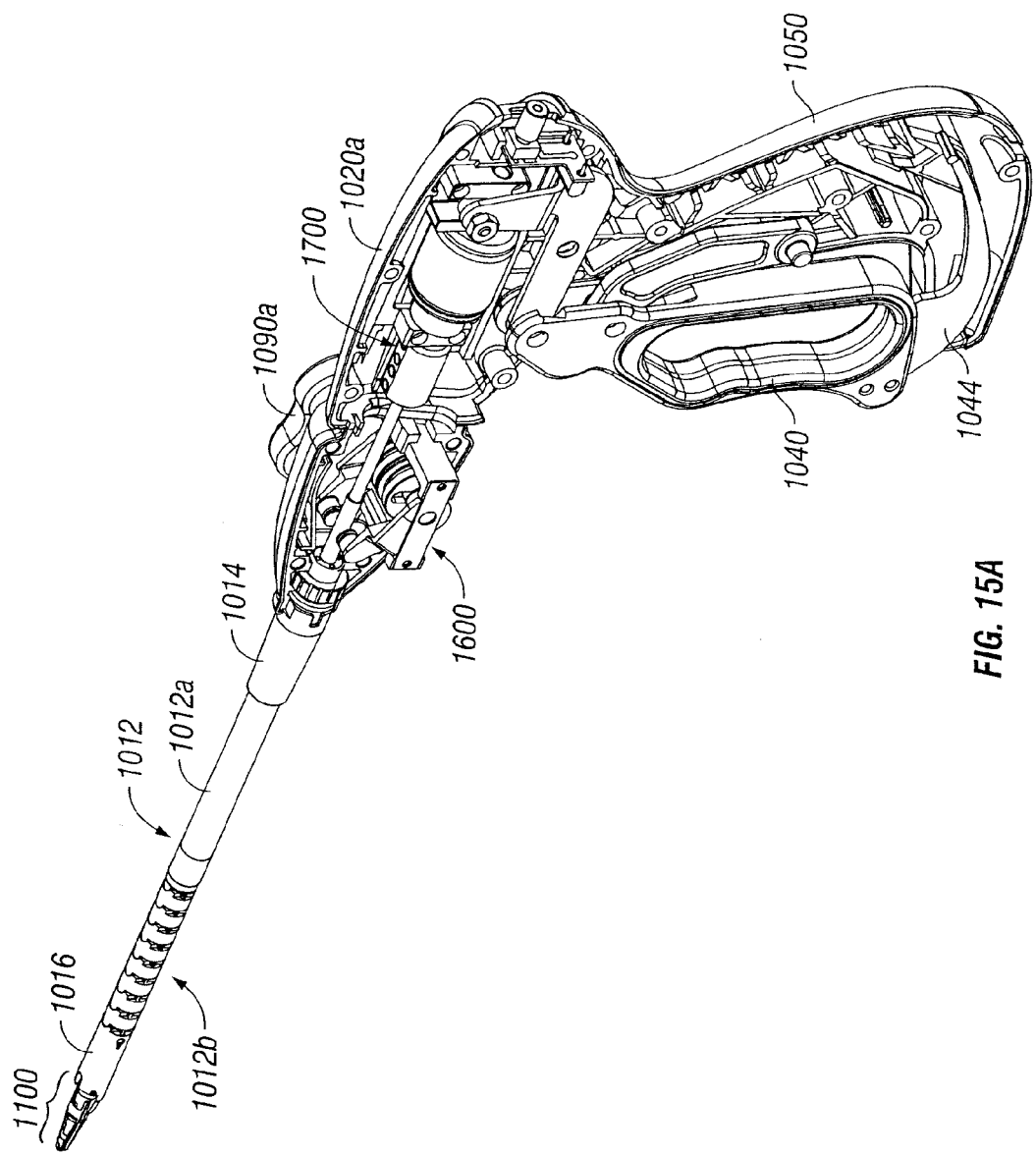
FIG. 15A is a rear perspective of the housing showing various internal components disposed therein.
Figure 15B:
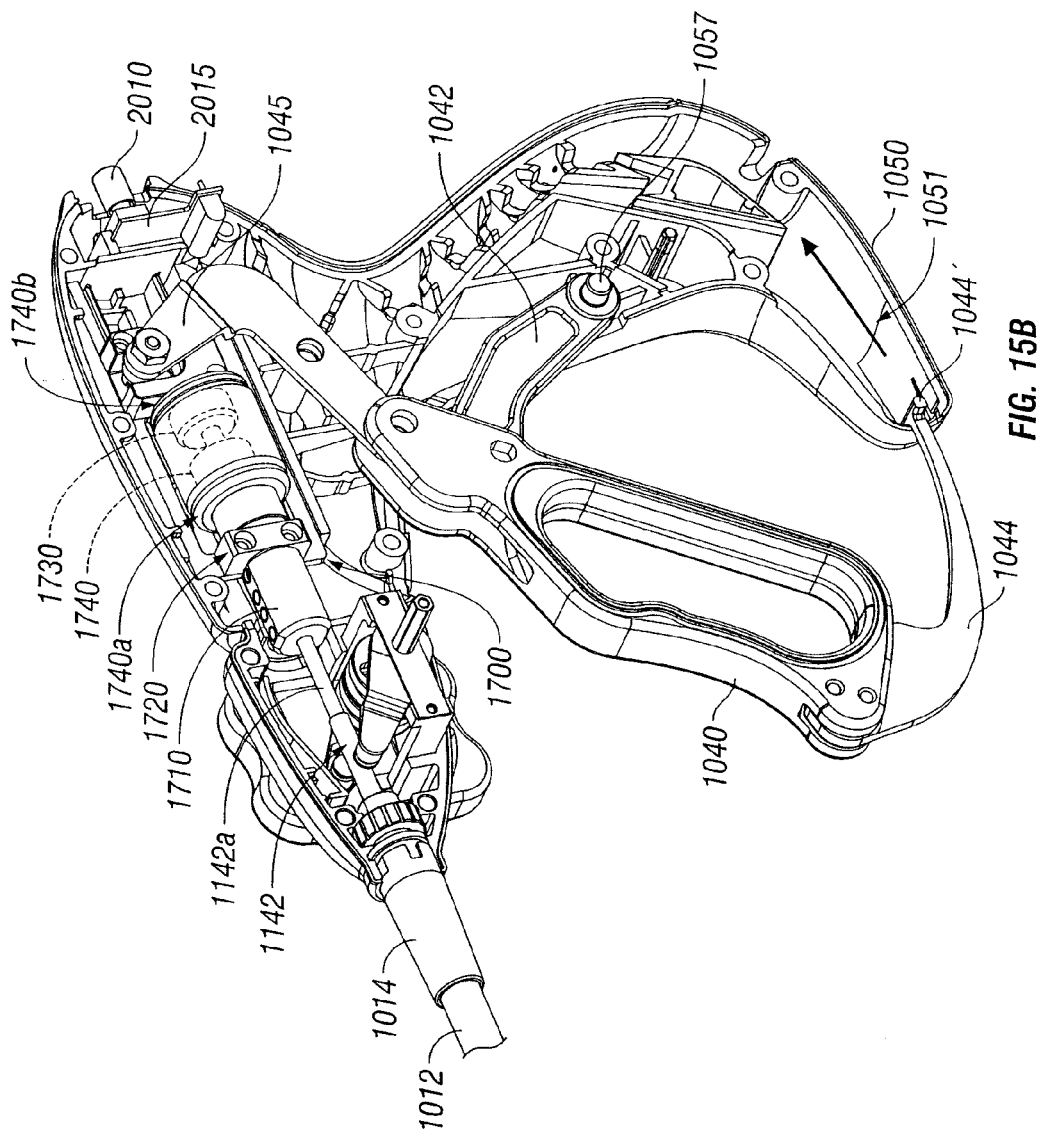
FIG. 15B is a front perspective of the housing showing various internal components disposed therein.

As best seen ion FIG. 14B, the drive assembly 1700 also includes a fine adjustment assembly 1061 operably associated with drive rod 1142 which allows a manufacturer to finely adjust the opening of the jaw members 1110 and 1120 relative to one another prior to final assembly. More particularly, the drive rod 1142 is connected to an adapter 1063 which, in turn, connects to drive rod 1142a connected to drive assembly 1700 as describe below. Adapter 1063 is threaded at a distal end thereof to threadably engage an adjustment knob 1067 to allow a manufacturer to finely adjust the length of the drive rode 1142 relative to the drive assembly 1700 thereby allowing the relative separation distance of the jaw members 1110 and 1120 to be accurately and finely controlled.

As best shown in FIGS. 14C, 15A, 15B, 19A and 19B, actuation of the drive assembly 1700 allows a user to selectively open and close the jaw members 1110 and 1120 to grasp and seal tissue. More particularly, the drive assembly 1700 includes a frame block 1800 which operably mounts a compression spring 1740 that biases the drive rod 1142 and coupling drive rod 1142a thereagainst. The coupling drive rod 1142a mounts to a drive block 1710 which, in turn, is coupled to the distal end of frame block 1800 by adapter 1720. When assembled, the frame block 1800 is disposed between opposing rails 1021 defined in housing halves 1020a and 1020b (See FIG. 14C) which permit the frame block 1800 to move within the housing 1020 upon actuation of handle 1040. Spring 1740 is mounted between a spacer 1730 (disposed adjacent adapter block 1720) and the proximal end 1810 of frame block 1800. A drive pin 1750 mounts to the opposite end of drive block 1710 and supports the compression spring 1740 to enable movement of the drive rod 1142.

Figure 19A:
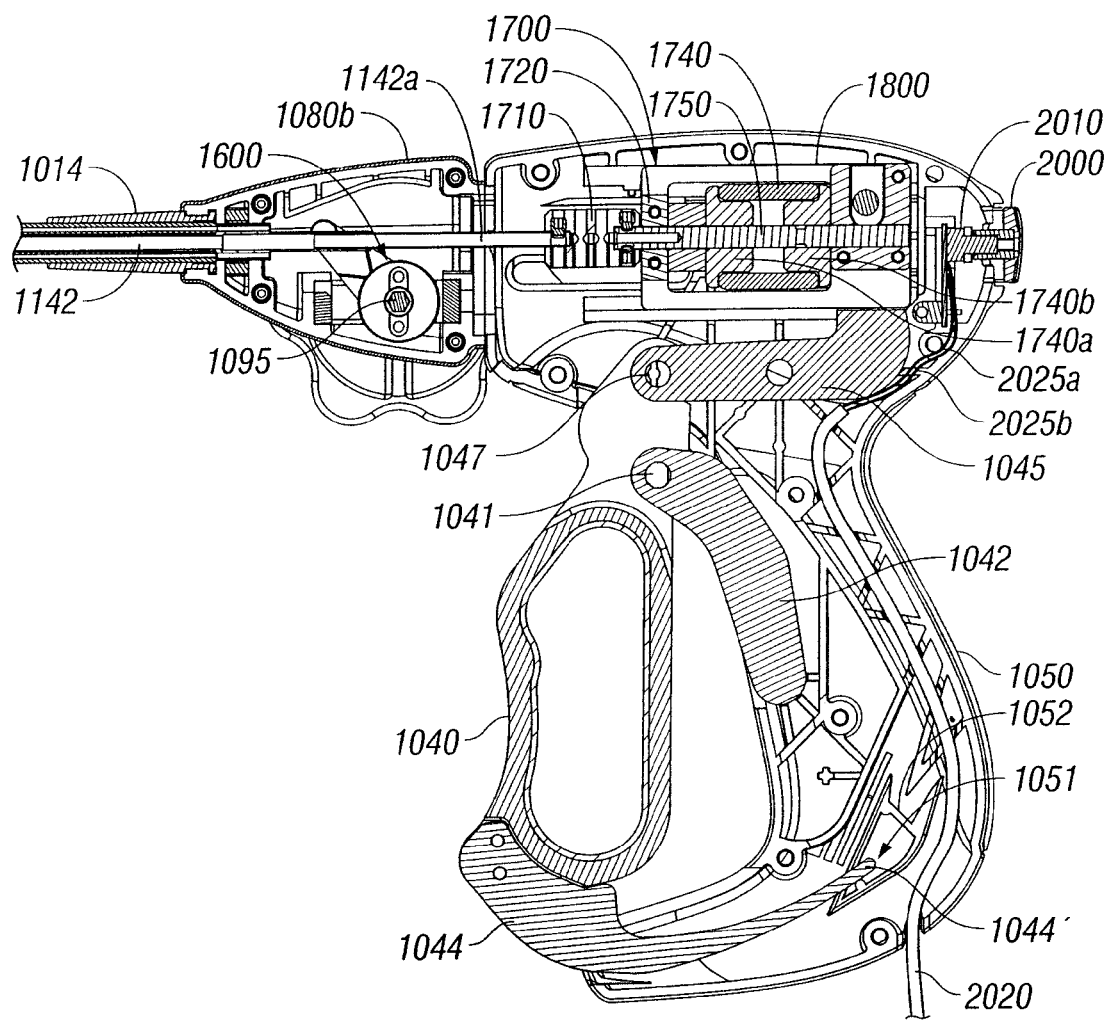
FIG. 19A is a side cross section of the housing showing the forceps in a substantially closed orientation.
Figure 19B:
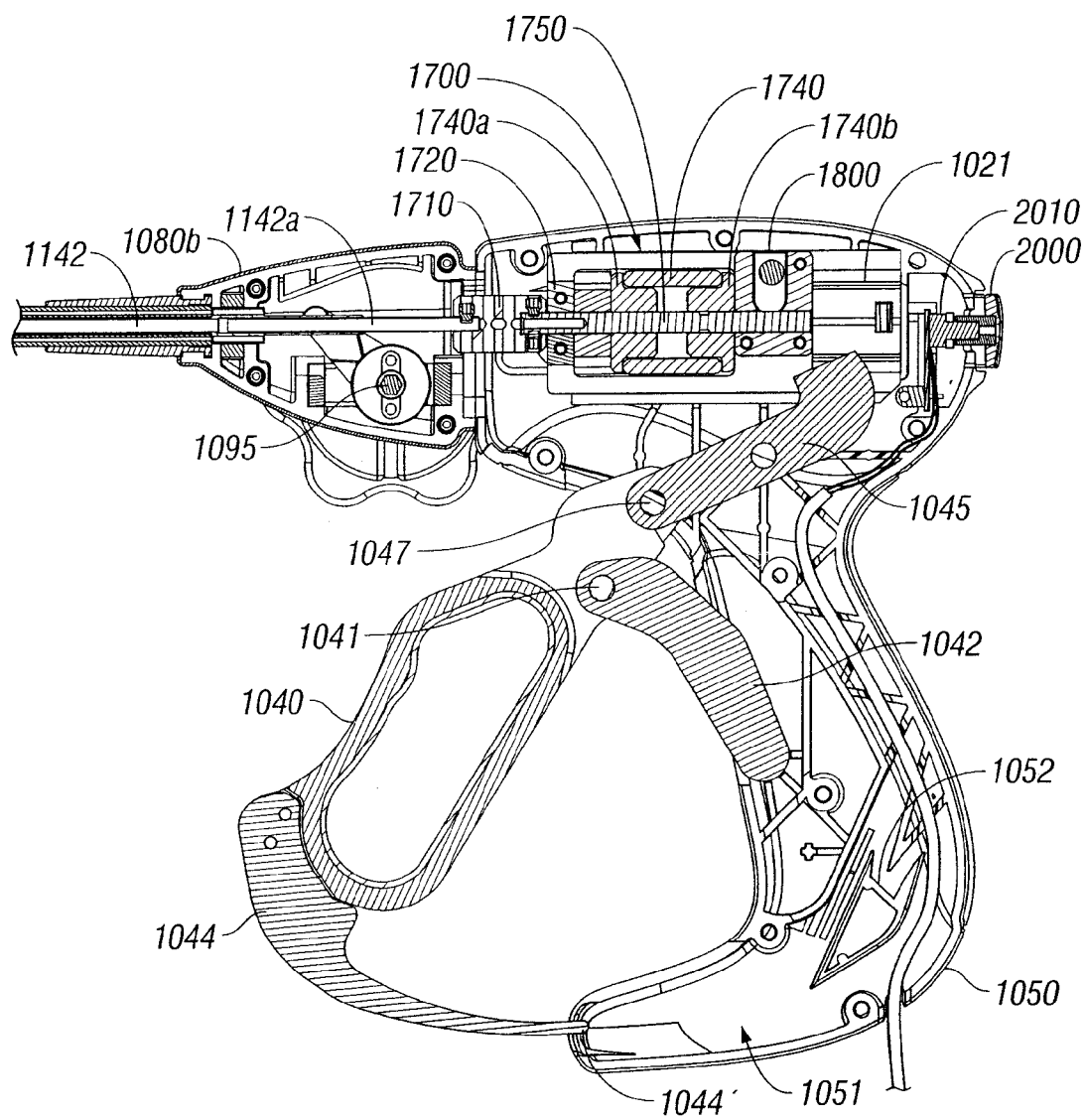
FIG. 19B is a side cross section of the housing showing the forceps in a substantially open orientation.
Figure 20A:
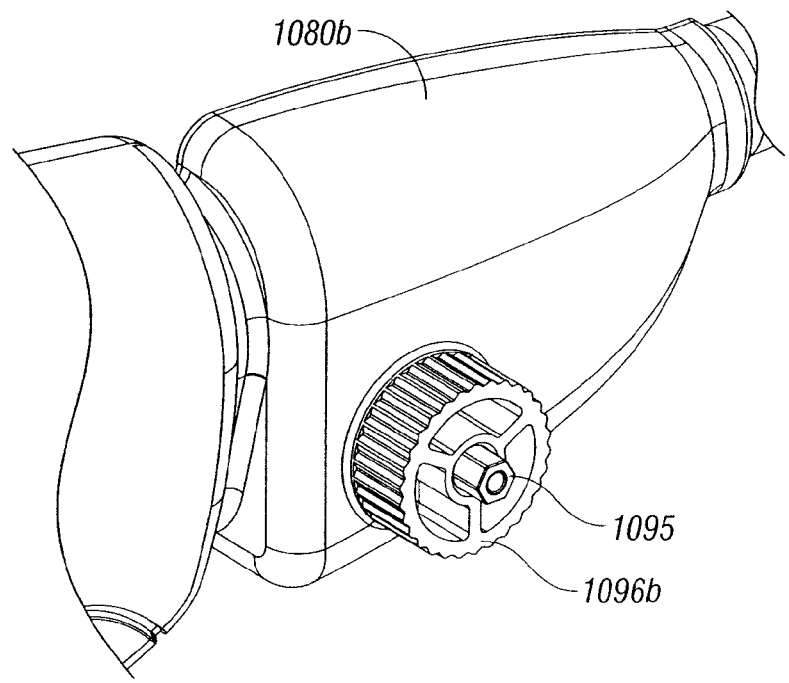
FIGS. 20A-20B are enlarged side perspective views of a gear member and articulation wheel of the articulation assembly.
Figure 20B:
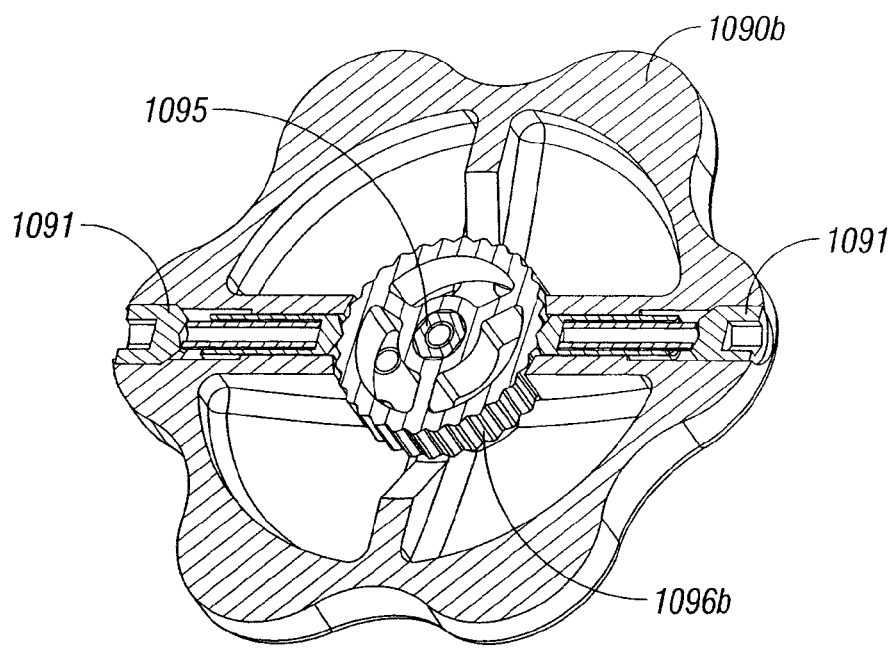

As mentioned above, handle 1040 is operable mounted to the drive assembly 1700 such that movement of the handle 1040 relative to handle 1050 translates the drive rod 1142 to open and close the jaw members 1110 and 1120. More particularly, handle 1040 is mounted at a top or distal end thereof via pin 1047 to link 1045 which, in turn, mounts to frame block 1800 also via pin 1047. Handle 1040 is also mounted to link 1042 at pivot point 1041 which, in turn, mounts to handle 1050 at pivot 1057 to complete the four bar mechanical assembly. As best shown in the comparison of FIGS. 19A and 19B, movement of handle 1040 towards handle 1050 rotates the two links 1042 and 1045 to force the frame block 1800 proximally and pull the drive rod 1142a proximally (which pulls drive rod 1142 proximally) to close the jaw members 1110 and 1120. A the same time, flange 1044 operably coupled to the bottom of handle 1040, reciprocates into a guide channel 1051 defined in handle 1050 such that a t-shaped end 1044' locks the handle 1040 in place relative to handle 1050. Flange 1044 and channel 1051 operate in a similar manner as described above with respect to forceps 10.

Spring 1740 includes two opposing compression discs 1740a and 1740b disposed therein which slidingly mount atop drive pin 1750. Upon movement to of handle 1040 towards handle 1050, spring disc 1740a is forced by movement of adapter 1720 to compress atop drive pin 1750 and pull the drive rod 1142 proximally. As mentioned above, movement of the drive rod 1142 proximally, causes the drive sleeve 1230 to engage flange 1113 of jaw member 1110 and close jaw members 1110 relative to jaw member 1120. Flange 1044 thereafter locks the handle 1040 relative to handle 1050 by virtue of the t-shaped end 1044' engaging a catch basin 1052 defined in the handle 1050. Upon re-grasping of handle 1040, the t-shaped end 1044' on flange 1044 is redirected out of channel 1051 to free handle 1040 for movement away from handle 1050. Spring 1740 biases the handle 1040 in an open orientation.

As mentioned above, jaw member 1120 may include a series of stop members 750 disposed on the inner facing surfaces of the electrically conductive sealing surface 1122 to facilitate gripping and manipulation of tissue and to define a gap "G" (see FIG. 17A) between opposing jaw members 1110 and 1120 during sealing and cutting of tissue. The preferred gap "G" between the conductive sealing surfaces 1112 and 1122 to effectively and reliably seal tissue is between about 0.001 and about 0.006 inches. The stop members 750 may be disposed in any configuration along the electrically conductive jaw surfaces 1112 and 1122 depending upon a particular jaw configuration or desired surgical result.

The end effector assembly 1100 may also be articulated in either direction (See arrow "B-B") as shown with reference to FIG. 18A. Once the tissue is grasped (within the required pressure range of about 3 kg/cm² to about 16 kg/cm²), the user then selectively applies electrosurgical energy to effectively seal tissue. Once sealed, the user may then selectively advances a knife (not shown) by actuating a trigger assembly (not shown) to cut the tissue along the tissue seal. The operating features and relative movements of one envisioned knife and trigger assembly are described above and also described with reference to U.S. patent application Ser. No. 10/460,926, the entire contents being incorporated herein.

Similar to FIGS. 2 and 3 above, the forceps 1000 includes a plurality of joints 1312 which are nestingly arranged in series to form flexible shaft 1012b. The distal end or coupling assembly 1016 mechanically engages the end effector assembly 1100 and the proximal end 1014 of the shaft 1012 mechanically engages the housing 1020. Each of the plurality of joints 1312 of the flexible shaft 1012b includes a distal knuckle 1312a and a proximal clevis 1312b formed therewith. Each knuckle 1312a operatively engages a clevis 1312b of an adjacent joint 1312a. Each joint 1312 has a central lumen 1317 defined therein and a pair of opposed lumens 1315a and 1315b formed on either side of central lumen 1317. The articulation cables 1094a and 1094b slideably extend through respective lumens 1315a and 1315b of joints 1312. The operation of cables 1094a and 1094b is explained above. The articulation cables 1094a and 1094b are preferably made from a flexible, friction-reducing material.

A switch 2000 is included which may conform to the outer shape of housing 1020 (once assembled). It is envisioned that the switch 2000 permits the user to selectively activate the forceps 1000 in a variety of different orientations, i.e., multi-oriented activation. As can be appreciated, this simplifies activation. A push button 2010 extends distally and engages a toggle plate 2015 (See FIG. 15B) which, in turn, connects to an electrical interface or PC Board (not shown). Electrical leads 2025a and 2025b internally disposed in cable 2020 (See FIG. 19) electrically connect to electrical interface or PC board. When the push button 2010 is depressed, the leads 2025a and 2025b carry electrical potentials to the jaw members 1110 and 1120.

It is envisioned that a safety switch or circuit (not shown) may be employed such that the switch cannot fire unless the jaw members 1110 and 1120 are closed and/or unless the jaw members 1110 and 1120 have tissue held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. U.S. patent application Ser. No. 10/427,832 describes one such feedback system, the entire contents of which being incorporated by reference herein.

Various handles and/or handle assemblies may be operatively connected or otherwise associated with end effector assembly 1100 in order to effect operation and movement of the various components thereof, i.e., drive rod 1142 and/or articulation cables 1094a, 1094b. Exemplary handles and/or handle assemblies for use with end effector 1100 are disclosed in U.S. Provisional Application Ser. No. 60/849,562 filed on Oct. 5, 2006, entitled "PROGRAMMABLE HANDLE ASSEMBLY FOR SURGICAL DEVICES"; and U.S. Provisional Application Ser. No. 60/849,560 filed on Oct. 5, 2006, entitled "HANDLE ASSEMBLY FOR ARTICULATED ENDOSCOPIC INSTRUMENTS", the entire disclosures of each of which being incorporated herein by reference.

From the foregoing and with reference to the various figure drawings, those skilled in the art will appreciate that certain modifications can also be made to the present disclosure without departing from the scope of the same. For example, it is contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Examples of such sensor systems are described in commonly-owned U.S. patent application Ser. No. 10/427,832 entitled "METHOD AND SYSTEM FOR CONTROLLING OUTPUT OF RF MEDICAL GENERATOR" filed on May 1, 2003 the entire contents of which are hereby incorporated by reference herein.

As can be appreciated, locating the switch 400, 2000 on the forceps 10, 1000 has many advantages. For example, the switch 400, 2000 reduces the amount of electrical cable in the operating room and eliminates the possibility of activating the wrong instrument during a surgical procedure due to "line-of-sight" activation. Moreover, it is envisioned that the switch 400, 2000 may be decommissioned during activation of the knife 185. Decommissioning the switch 400, 2000 when the trigger is actuated eliminates unintentionally activating the forceps 10, 1000 during the cutting process. It is also envisioned that the switch 400, 2000 may be disposed on another part of the forceps 10, 1000, e.g., the handle 40, 1040, rotating assembly 80, housing 20, etc.

Another envisioned safety mechanism would be to route one of he cable leads to energize the one jaw member, e.g., jaw member 1120, and the other electrical potential may be conducted through a drive sleeve, e.g., drive sleeve 1230, surrounding drive rod 1142 and transferred to the other jaw member 1110 to establish electrical continuity only upon retraction of the drive sleeve. It is envisioned that this particular envisioned embodiment will provide at least one additional safety feature, i.e., electrical continuity to the jaw members 1110 and 1120 is made only when the jaw members 1110 and 1120 are closed. The drive rod 1142 may also be energized to the second electrical potential and include a similar-type safety mechanism.

In one envisioned embodiment, the knife 185 may not be included with the forceps 10, 1000 and the instrument is designed solely for sealing vessels or other tissue bundles. In this instance, the camming hub 144 (with respect to forceps 10 only) may be rotated to articulate the end effector assembly 100 and cables 94a and 94b may be eliminated.

In one embodiment, two isolated electrical leads may supply electrical energy to respective jaw members 110 and 120 (or 1110 and 1120). In this instance it may be desirable to provide a channel along the outside of shaft 12, 1012 which guides the electrical leads from the housing 20, 1020 to the individual jaw members 110, 120 (or 1110 and 1120) One or more wire crimps or the like may be utilized to hold the electrical leads in place. Alternatively, cables 94a and 94b (or 1094a and 1094b) may be utilized to both articulate the end effector assembly 100 (or 1100) and to supply electrical energy to the jaw members 110 and 120 (or 1110 and 1120).

With particular respect to forceps 10 in particular but nor exclusively, the cable lead, e.g., cable lead 311 of forceps 10 is held loosely but securely along the cable path to permit rotation of the jaw member 110 about pivot 103. The two potentials are isolated from one another by virtue of the insulative sheathing surrounding cable lead 311. Moreover, the proximal portion of shaft 12 may be rigid or substantially rigid and the distal portion is flexible and/or articulateable in the manner described in more detail above. Alternatively, the entire shaft 12 may be flexible. Still further, the trigger assembly 70 may be prevented from firing until movable handle 40 is locked (or simply moved) proximally to close the jaw members 110 and 120.

In embodiment relating to both forceps 10, 1000, the electrically conductive sealing surfaces 112,122 and 1112, 1122 of the jaw members 110, 120 and 1110, 1120, respectively, are relatively flat to avoid current concentrations at sharp edges and to avoid arcing between high points. In addition and due to the reaction force of the tissue when engaged, jaw members 110, 120 and 1110, 1120 can be manufactured to resist bending. For example, the jaw members 110, 120 and 1110, 1120 may be tapered along the width thereof which resists bending due to the reaction force of the tissue.

It is envisioned that the outer surface of the end effector assembly 100, 1100 may include a nickel-based material, coating, stamping, metal injection molding which is designed to reduce adhesion between the jaw members 110, 120 and 1110, 1120 with the surrounding tissue during activation and sealing. Moreover, it is also contemplated that the conductive surfaces 112, 122 and 1112 and 1122 of the jaw members 110, 120 and 1110, 1120, respectively, may be manufactured from one (or a combination of one or more) of the following materials: nickel-chrome, chromium nitride, MedCoat 2000 manufactured by The Electrolizing Corporation of OHIO, inconel 600 and tin-nickel. The tissue conductive surfaces 112, 122 and 1112 and 1122 may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112, 122 and 1112 and 1122 made from or coated with Ni200, Ni201 (~100% Ni) also showed improved non-stick performance over typical bipolar stainless steel electrodes.

Forceps 10, 1000 may be designed such that it is fully or partially disposable depending upon a particular purpose or to achieve a particular result. For example, end effector assembly 100, 1100 may be selectively and releasably engageable with the distal end of the shaft 12, 1012 and/or the proximal end 14, 1014 of shafts 12, 1012 may be selectively and releasably engageable with the housing 20, 1020. In either of these two instances, the forceps 10, 1000 would be considered "partially disposable" or "reposable", i.e., a new or different end effector assembly 100, 1100 (or end effector assembly 100, 1100 and shaft 12, 1012) selectively replaces the old end effector assembly 100, 1100 as needed. As can be appreciated, the presently disclosed electrical connections would have to be altered to modify the instrument to a reposable forceps.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument for treating tissue, comprising:
    a housing having a flexible shaft extending therefrom having an axis A-A defined therethrough, the shaft including first and second jaw members attached at a distal end thereof, each jaw member including an electrically conductive tissue contacting surface adapted to connect to a source of electrosurgical energy such that the electrically conductive tissue contacting surfaces are capable of conducting electrosurgical energy through tissue held therebetween;
    a drive assembly disposed in the housing including a first actuator operably coupled to a drive rod for reciprocation thereof and a second actuator operably coupled to the drive rod for rotation thereof;
    a knife operably coupled to a distal end of the drive rod; and
    a cam assembly coupled to the distal end of the drive rod configured to translate the knife relative to the jaw members,
    wherein actuation of the first actuator moves the jaw members from a first position in spaced relation to one another to a second position closer to one another for engaging tissue and actuation of the second actuator rotates the drive rod about the axis A-A to translate the knife in an axial direction with respect to the axis A-A to cut tissue disposed between the jaw members.

2. An electrosurgical instrument for treating tissue according to claim 1 wherein the cam assembly includes a camming hub having a grooved outer periphery defined therein which is configured to matingly engage a corresponding detent disposed on the knife wherein rotational movement of the drive rod correspondingly rotates the camming hub which, in turn, translates the detent and knife relative to the jaw members.

3. An electrosurgical instrument for treating tissue according to claim 2 wherein the cam assembly also includes a coupling device configured to couple the drive rod to the camming hub.

4. An electrosurgical instrument for treating tissue according to claim 3 wherein the coupling device includes a keyed rod configured at one end to interface with the drive rod and configured at an opposite end to matingly engage a key-like aperture defined in the camming hub.

5. An electrosurgical instrument for treating tissue according to claim 1 wherein the flexible shaft includes a plurality of joints nestingly arranged in series to form at least a portion of the flexible shaft.

6. An electrosurgical instrument for treating tissue according to claim 5 wherein each joint includes at least one lumen defined therethrough for allowing reciprocation of the drive rod therein.

7. An electrosurgical instrument for treating tissue according to claim 5 wherein each joint includes a central lumen formed therein and a pair of opposed lumens formed on either side of the central lumen and wherein the electrosurgical instrument includes a pair of articulation cables slideably extendable through the respective opposed lumens which are moveable relative to one another to articulate the shaft relative to axis A-A.

8. An electrosurgical instrument for treating tissue according to claim 7 further comprising a third actuator operably coupled to the housing for moving the pair of articulation cables relative to one another to articulate the flexible shaft relative to axis A-A.

9. An electrosurgical instrument for treating tissue, comprising:
   a housing having a flexible shaft extending therefrom including an axis A-A defined therethrough;
   an end effector assembly attached at the distal end of the shaft, the end effector including a clevis which supports first and second jaw members about a pivot pin such that the jaw members are moveable between a first spaced apart position relative to one another to a second position in closer relation relative to one another, each jaw member including an electrically conductive tissue contacting surface adapted to connect to a source of electrosurgical energy such that the electrically conductive tissue contacting surfaces are capable of conducting electrosurgical energy through tissue held therebetween, the jaw members each including an angled cam surface defined therein and the clevis including a slot defined therein;
   a knife operably coupled to a distal end of the drive rod;
   a drive assembly disposed in the housing including a first actuator operably coupled to a drive rod for reciprocation thereof and a second actuator operably coupled to the drive rod for rotation thereof, the distal end of the drive rod configured to receive a drive pin which engages both the cam surface defined in the jaw members and the slot defined in the clevis such that actuation of the first actuator reciprocates the drive pin to move the jaw members from a first position in spaced relation to one another to a second position closer to one another for engaging tissue and actuation of the second actuator rotates the drive rod about the axis A-A to translate the knife in an axial direction with respect to the axis A-A to cut tissue disposed between the jaw members; and
   a cam assembly coupled to the distal end of the drive rod configured to translate the knife relative to the jaw members.

10. An electrosurgical instrument for treating tissue according to claim 9 wherein the cam assembly includes a camming hub having a grooved outer periphery defined therein which is configured to matingly engage a corresponding detent disposed on the knife wherein rotational movement of the drive rod correspondingly rotates the camming hub which, in turn, translates the detent and knife relative to the jaw members.

11. An electrosurgical instrument for treating tissue according to claim 10 wherein the drive rod is slidingly received within the camming hub 12. An electrosurgical instrument for treating tissue according to claim 10 wherein the cam assembly also includes a coupling device configured to couple the drive rod to the camming hub.

13. An electrosurgical instrument for treating tissue according to claim 12 wherein the coupling device includes a keyed rod configured at one end to interface with the drive rod and configured at an opposite end to matingly engage a key-like aperture defined in the camming hub.

14. An electrosurgical instrument for treating tissue according to claim 9 wherein the flexible shaft includes a plurality of joints nestingly arranged in series to form at least a portion of the flexible shaft.

15. An electrosurgical instrument for treating tissue according to claim 14 wherein each joint includes at least one lumen defined therethrough for allowing reciprocation of the drive rod therein.

16. An electrosurgical instrument for treating tissue according to claim 14 wherein each joint includes a central lumen formed therein and a pair of opposed lumens formed on either side of the central lumen and wherein the electrosurgical instrument includes a pair of articulation cables slideably extendable through the respective opposed lumens which are moveable relative to one another to articulate the shaft relative to axis A-A.

17. An electrosurgical instrument for treating tissue according to claim 16 further comprising a third actuator operably coupled to the housing for moving the pair of articulation cables relative to one another for articulating the flexible shaft relative to axis A-A.

* * * * *